US005556504A

United States Patent [19]
Rajala et al.

[11] Patent Number: 5,556,504
[45] Date of Patent: Sep. 17, 1996

[54] APPARATUS FOR PLACING DISCRETE PARTS TRANSVERSELY ONTO A MOVING WEB

[75] Inventors: Gregory J. Rajala; Paul M. Niemi; Daniel J. Oshefsky, all of Neenah, Wis.

[73] Assignee: Kimberly-Clark Corporation, Neenah, Wis.

[21] Appl. No.: 459,606

[22] Filed: Jun. 2, 1995

Related U.S. Application Data

[60] Division of Ser. No. 381,364, Jan. 31, 1995, which is a continuation-in-part of Ser. No. 186,352, Jan. 25, 1994.

[51] Int. Cl.$^6$ ................................................. B32B 31/00
[52] U.S. Cl. .................... 156/519; 156/552; 156/303; 414/757; 414/758
[58] Field of Search .................... 156/164, 303, 156/519, 552, 362, 540, 541, 568; 414/757, 758

[56] References Cited

U.S. PATENT DOCUMENTS

| | | | |
|---|---|---|---|
| 3,728,191 | 4/1973 | Wierzba et al. | 156/265 |
| 4,081,301 | 3/1978 | Buell | 156/164 |
| 4,293,367 | 10/1981 | Klasek et al. | 156/494 |
| 4,394,898 | 7/1983 | Campbell | 198/374 |
| 4,608,115 | 8/1986 | Schroth et al. | 156/519 |
| 4,617,082 | 10/1986 | Oshefsky et al. | 156/447 |
| 4,786,346 | 11/1988 | Ales et al. | 156/160 |
| 4,801,345 | 1/1989 | Dussaud et al. | 156/164 |
| 4,838,969 | 6/1989 | Nomura et al. | 156/160 |
| 4,854,989 | 8/1989 | Singheimer | 156/161 |
| 4,915,767 | 4/1990 | Rajala et al. | 156/440 |
| 4,917,746 | 4/1990 | Kons et al. | 156/164 |
| 4,941,939 | 7/1990 | Nomura et al. | 156/495 |
| 4,946,539 | 8/1990 | Ales et al. | 156/495 |
| 5,080,741 | 1/1992 | Nomura et al. | 156/201 |
| 5,091,039 | 2/1992 | Ujimoto et al. | 156/519 |
| 5,147,487 | 9/1992 | Nomura et al. | 156/164 |
| 5,213,645 | 5/1993 | Nomura et al. | 156/164 |
| 5,221,390 | 6/1993 | Persson et al. | 156/164 |
| 5,236,539 | 8/1993 | Rogberg et al. | 156/495 |
| 5,275,676 | 1/1994 | Rooyakkers et al. | 156/164 |

FOREIGN PATENT DOCUMENTS

| | | |
|---|---|---|
| 4-28363 | 1/1992 | Japan . |
| 4-28364 | 1/1992 | Japan . |
| 2248380 | 4/1992 | United Kingdom . |

*Primary Examiner*—Michael W. Ball
*Assistant Examiner*—Sam Chuan Yao
*Attorney, Agent, or Firm*—Donald L. Traut; Mark L. Davis

[57] ABSTRACT

This invention pertains to processing continuous webs such as paper, film, composites, and the like, in dynamic continuous processing operations. More particularly, it relates to transferring discrete parts to a continuous web, whether paper, film, composite, or the like. Specifically, the invention relates to methods and apparatus for taking discrete parts from a source in a taking zone, optionally taking the discrete parts as components of a continuous web, onto a transport head on a transfer assembly, severing the discrete parts from the continuous web if received as part of a continuous web, rotating the transfer assembly about a first axis and correspondingly rotating the transport head about a second axis radial to the first axis, to thereby present the discrete parts to a receiver in a transfer zone, and transferring the discrete parts to the receiver in the transfer zone. The invention includes using a roughened taking section on the transport head, interacting with textured surface on the discrete parts, to hold the discrete parts to the transport head, with optional use of suction through the transport head to assist in holding the discrete parts to the transport head. Novel apparatus is included for delivering suction to and through rotating slip rings.

14 Claims, 14 Drawing Sheets

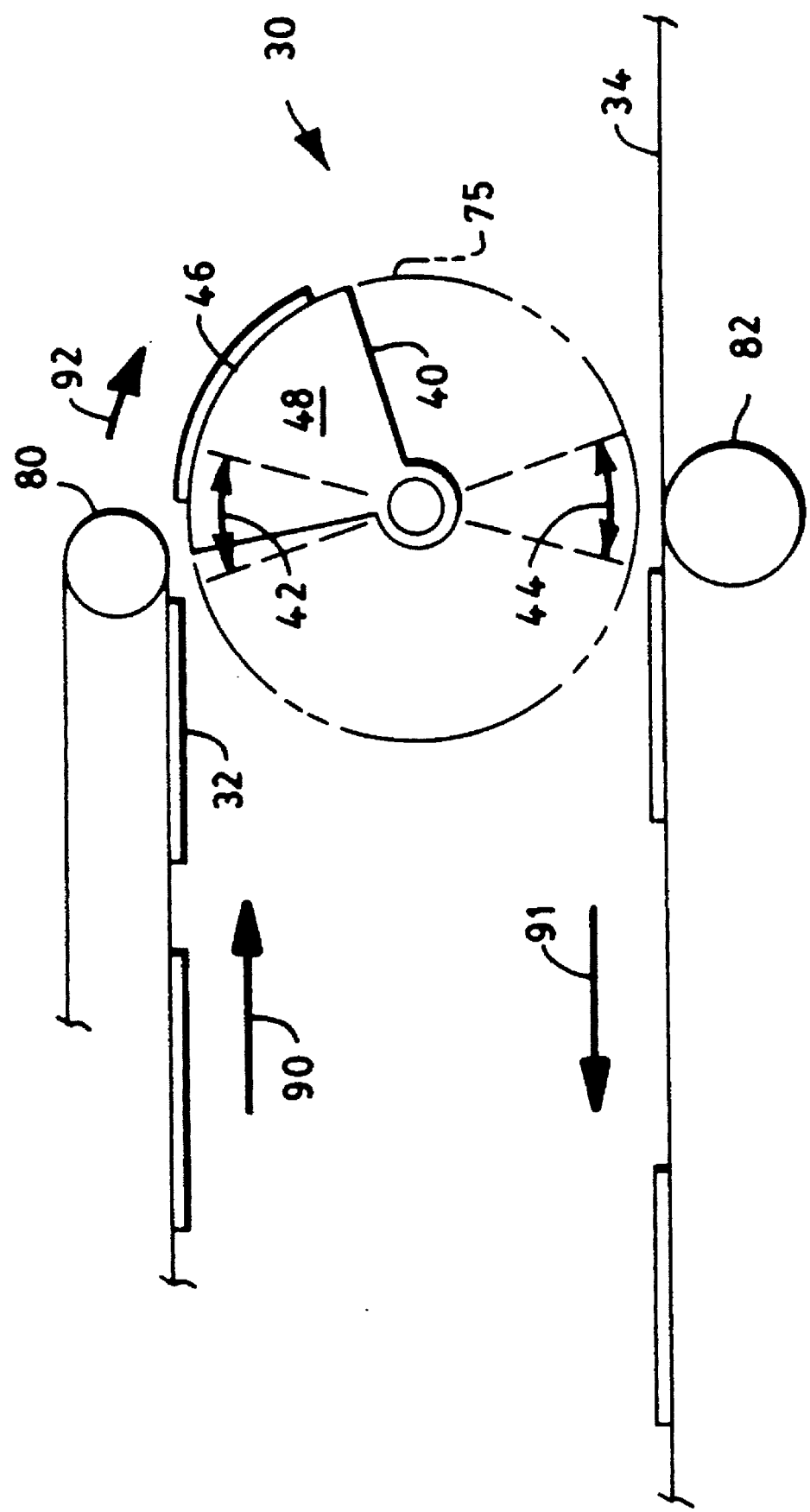

5,556,504

APPARATUS FOR PLACING DISCRETE PARTS TRANSVERSELY ONTO A MOVING WEB

This is a divisional application of application U.S. Ser. No. 08/381,364, filed on Jan. 31, 1995, which is a CIP of Ser. No. 08/186,352 filed on Jan. 25, 1994.

Priority is claimed under 35 U.S.C. 120 with respect to application Ser. No. 08/186,352, filed Jan. 25, 1994, herein incorporated by reference.

FIELD OF THE INVENTION

The present invention relates to a method and apparatus, for receiving discrete parts travelling at a speed and applying the parts to a web travelling at a different speed. The invention more particularly concerns a method and apparatus for receiving discrete parts of a continuously moving web of material travelling at a certain speed and applying the parts to a second continuously moving web travelling at a different speed.

BACKGROUND OF THE INVENTION

Articles, such as disposable diapers, generally have been manufactured by a process where discrete parts or components of different materials, such as leg elastic, waist elastic, tapes and other fasteners such as hook and loop materials or snaps, have been applied to a continuously moving product web. Often, the speed at which the parts are fed into the process is not the same as the speed of the product web itself. Thus, the speed, and in some cases the orientation, of the parts must be changed to match the speed and orientation of the product web to properly apply the parts without adversely affecting the process or the finished product.

Several different conventional methods for changing the speed of a part or component of material such that it can be applied to a continuously moving web have been known to those skilled in the art.

For example, one method has been known as the slip gap or slip cut method. A web of material, which is travelling at a slower speed than the moving web, is fed into a knife and anvil roll having a surface speed equal to the speed of the moving web. As the material is cut into discrete parts, vacuum in the anvil roll is activated to draw the parts of material to the surface of the anvil roll. The anvil roll then carries the parts to the moving web where the vacuum is released and the parts are applied to the moving web while both the parts and the moving web are travelling at the same speed.

Another method has utilized festoons to reduce the speed of the moving web to match the speed of the discrete parts of material to be applied to the web. The moving web is temporarily slowed down to the speed of the parts with the excess portion of the moving web gathering in festoons. The parts of material are then applied to the moving web while both the parts and the web are travelling at the same speed. The festoons are then released allowing the moving web to return to its original speed.

Another method has utilized a slider-crank mechanism to accomplish the speed change. The slider-crank mechanism utilizes concentrically mounted arms or linkages to receive the discrete parts of material, increase the speed of the parts to match the speed of the moving web and apply the parts to the moving web. The slider-crank mechanism is a special case of a four bar linkage system.

Finally, another such method to change the speed of a discrete part before it is applied to a moving web has utilized a cam actuated crank-follower mechanism. The cam actuated crank-follower mechanism comprises levers that are mounted on a rotatable driving plate. Each lever has a pivot point and includes a cam follower on one end and a drag link on the other end. An applicator device is connected to the other end of the drag link. The cam follower remains in contact with a fixed cam that is mounted concentric with the driving plate's center of rotation. As the driving plate rotates, the levers pivot as their cam followers follow the cam shape. As the levers pivot, the applicator devices are caused to speed up or slow down. Thus, the mechanism can be designed to receive discrete parts of material, change the speed of the parts and apply the parts to a moving web. An example of this method is described in U.S. Pat. No. 4,610,751 issued Sep. 9, 1986, to Eschler.

Conventional methods, such as those described above, have exhibited several drawbacks. First, as the discrete parts of material are transferred, they are often subjected to a tugging action because the surface speed of the transfer means used to transfer the parts is greater than the speed of the parts. The tugging action may result in an elongation or tear of the parts. Second, several of the conventional methods provide substantial speed variations but do not provide any periods where the speed remains constant for a fixed duration. Thus, the discrete parts may be adversely affected because the surface speed of the transfer means used to transfer the parts is continuously changing during the receiving and application process. Finally, several of the conventional methods can be very expensive and time consuming to change as the size and speed of the discrete parts and the speed of the moving web change to coincide with various finished product sizes. Consequently, an inexpensive and adaptable method for receiving discrete parts travelling at a first speed and applying the parts to a web travelling at a different second speed is desirable.

Moreover, it is desirable that the receiving and applying of the parts occurs while the respective surface speeds are maintained substantially constant for a fixed duration. For example, it is desirable to apply the parts to the substrate web while the parts and substrate web are travelling at substantially the same surface speed. A constant speed dwell allows precise control of the length and placement of the part on the substrate web especially if the part is fragile and/or elastic.

Specifically, this invention relates to taking, transferring, and presenting discrete parts including internally-contained elastics elements; and especially handling such discrete parts while the elongation in the elastics elements is maintained, with little or no snap-back of the elongation.

It is an object of this invention to provide methods and apparatus for taking the discrete parts at a first speed onto a transport head, rotating the transport head and the discrete parts about a first axis at a variable radial speed, and rotating the transport head about a second axis radial to the first axis.

It is another object to provide methods and apparatus for taking the discrete parts onto the transport head while an arcuate top wall of the transport head is disposed transverse to the direction of travel of the discrete parts being received.

It is a further object to provide methods and apparatus for holding the discrete parts on the transport head by providing a toughened surface on the transport head, and a cooperating textured surface on the discrete parts.

It is yet another object to provide methods and apparatus for applying suction to the transport head through a central tubular conduit, a slip ring about the conduit, and cooperating first and second arrays of suction ports in the slip ring and conduit to effect suction to the transport head.

SUMMARY OF THE INVENTION

This invention describes apparatus and methods for receiving discrete parts, optionally as part of a continuous web, and transferring the discrete parts, separated from the web, onto a receiver.

In a first family of embodiments, the invention contemplates a method for taking discrete parts travelling at a first speed in a first direction, and transferring the discrete parts to a receiver travelling at a second speed in a second direction, the method comprising the steps of providing a rotatable transfer assembly, and at least one transport head mounted on the transfer assembly, for taking the discrete parts onto the at least one transport head in a taking zone, and for transferring the discrete parts to the receiver in a transfer zone; taking a discrete part onto the at least one transport head in the taking zone wherein a leading edge of the discrete part is oriented at a first angle "A" with respect to the first direction of travel; after taking the discrete part onto the at least one transport head, (i) rotating the rotatable transfer assembly about a first axis oriented in a third direction transverse to, and disposed in a plane parallel with, the first direction, at a variable angular velocity such that the at least one transport head travels at a first surface speed which substantially equals the first speed of the discrete part as the discrete part is taken onto the at least one transport head in the taking zone, and travels at a second surface speed which substantially equals the second speed of the receiver as the discrete part is transferred to the receiver in the transfer zone, the rotating of the rotatable transfer assembly defining an orbital path, and (ii) rotating the transport head about a second radial axis intersecting the first axis and extending outwardly therefrom, to thereby orient the leading edge of the discrete part at an angle "B" measured with respect to the second direction of travel of the receiver in the transfer zone, different from angle "A"; and transferring the so rotated discrete part to the receiver in the transfer zone.

The method preferably includes rotating the rotatable transfer assembly about the first axis while simultaneously rotating the transport head about the second radial axis.

The method contemplates taking the discrete part onto the transport head as part of, and contained in, a continuous web, and cutting the web to separate out the discrete part after taking the discrete part onto the transport head and before rotating the transport head about the second radial axis.

Preferably, the method also includes providing, on the transport head, an area having a roughened surface, and providing, on the discrete part, a textured surface, that interacts with the area of toughened surface on the transport head to thereby secure the holding of the discrete part to the transport head.

The method can include providing suction of about 1 to about 80 inches of water, preferably at about 5 up to about 60 inches, more preferably about 45 inches of water, through the transport head to the discrete part, to enhance the holding of the discrete part to the transport head while rotating the rotatable transfer assembly from the taking zone to the transfer zone.

In preferred members of this first family of embodiments, the transport head has an arcuate top wall for receiving the discrete parts thereunto, the method including orienting the transport head such that the curvature of the arcuate top wall is disposed transverse to the first direction of travel at the taking zone, and rotating the transport head about the radial axis after taking the discrete part onto the transport head, and thereby aligning the arcuate top wall with the receiver at the transfer zone, whereby, after the rotation about the second radial axis, the arcuate top wall can, in the transfer zone, interact with a substantially planar receiver disposed tangential to the orbital path, along a line transverse to the second direction in the transfer zone, and interacts with the discrete parts in the taking zone along a line approximating the first direction.

The method further comprises taking the discrete part while the discrete part is elongated and under tension exerted by elastics integral with the discrete part, and including holding the discrete part to the transport head with sufficient force that, when elastics integral with the discrete part are elongated by e.g. 150%, in cooperation with a friction relationship between the transport head and the discrete part, the discrete part exhibits less than 50%, preferably less than 20%, more preferably less than 10%, snap-back of the elongation while the discrete part is held on the transport head.

In a second family of embodiments, the invention contemplates a method for taking discrete parts travelling in a first direction and applying the discrete parts to a receiver travelling in a second direction, the method comprising the steps of providing a rotatable transfer assembly, mounted for rotation in an orbital path about a first axis oriented in a plane parallel with the first direction, and at least one transport head mounted on the transfer assembly, for taking the discrete parts onto the at least one transport head in a taking zone, and for transferring the discrete parts to the receiver in a transfer zone, the transport head having an arcuate top wall, including arcuate curvature thereon, for taking the discrete parts, the transport head being mounted for rotation about a second radial axis extending outwardly from the first axis; orienting the transport head such that the curvature of the arcuate top wall is disposed transverse to the first direction of travel; while the arcuate top wall is so disposed transverse to the first direction of travel, taking a discrete part onto the at least one transport head in the taking zone; after taking the discrete part onto the at least one transport head, (i) rotating the rotatable transfer assembly about the first axis, and (ii) rotating the transport head, and the discrete part disposed thereon, about the second radial axis, to thereby bring the curvature of the arcuate top wall into alignment with the second direction of travel, and the transport head into proximity with the receiver in the transfer zone; and transferring the so rotated discrete part to the receiver.

The method preferably includes rotating the rotatable transfer assembly about the first axis while simultaneously rotating the transport head about the second radial axis, whereby, after the rotation about the second radial axis, the arcuate top wall can interact with a substantially planar receiver disposed tangential to the orbital path, along a line transverse to the second direction in the transfer zone, as well as interact with the discrete parts in the taking zone along a line approximating the first direction.

Preferably, the method of this second family of embodiments also includes providing, on the transport head, an area having a toughened surface, and providing, on the discrete part, a textured surface, the textured surface of the discrete part interacting with the area of toughened surface on the transport head to thereby secure the holding of the discrete part to the transport head.

The method preferably includes holding the discrete part to the transport head with suction while rotating the rotatable transfer assembly from the taking zone to the transfer zone, to enhance the holding of the discrete part to the transport head.

In a third family of embodiments, the invention contemplates apparatus for taking discrete parts travelling at a first speed in a first direction, and transferring the discrete parts to a receiver travelling at a second speed in a second direction, the apparatus comprising a transfer assembly mounted for rotation about a first axis oriented in a third direction transverse to, and disposed in a plane parallel with, the first direction; at least one transport head mounted on the transfer assembly, for taking the discrete parts onto the at least one transport head in a taking zone, wherein a leading edge of the discrete part is oriented at a first angle "A" with respect to the first direction of travel, and for transferring the discrete parts to the receiver in a transfer zone; a first driver, for driving the transfer assembly about the first axis, at a variable angular velocity such that the at least one transport head travels at a first surface speed which substantially equals the first speed of the discrete part as the discrete part is taken onto the at least one transport head in the taking zone, and travels at a second surface speed which substantially equals the second speed of the receiver as the discrete part is applied to the receiver in the transfer zone, the rotating of the transfer assembly thereby defining an orbital path; and a second driver for rotating the transport head about a second radial axis of rotation intersecting the first axis, and extending outwardly from the first axis, to thereby orient the leading edge of the discrete part at an angle "B" measured with respect to the second direction of travel of the receiver in the transfer zone, different in magnitude from angle "A".

In preferred embodiments, the second driver comprises the first driver in combination with control apparatus for causing rotation of the transport head about the second radial axis. In the alternative, the second driver comprises control apparatus, cooperating with motive force provided by the first driver, for causing the second driver to rotate the transport head about the second radial axis while the first driver drives the transfer assembly about the first axis.

The apparatus preferably includes suction apparatus for holding the discrete part to the transport head between the taking zone and the transfer zone, while the first driver drives the transfer assembly about the first axis.

Preferably, the transport head has a receiving area for taking the discrete parts, the receiving area having a toughened surface comprising a first base surface component, and a second component comprising a first array of protrusions extending outwardly at least about 0.006 millimeter, preferably up to about 3 millimeters, more preferably between about 0.01 millimeter and about 0.03 millimeter, from the base surface component for receiving the discrete parts thereunto, such that the protrusions on the receiving area can interact with a textured surface on the discrete part to thereby secure the discrete part to the transport head.

In a fourth family of embodiments, the invention contemplates a method of transferring discrete parts from a giver at a taking zone to a receiver at a transfer zone, the method comprising the steps of providing a transfer assembly, including at least one transport head mounted on the transfer assembly, the transport head having an outer wall for taking the discrete parts, and for releasing the discrete parts, the outer wall having at least one area having a roughened surface, the area comprising (i) a base surface component, and (ii) a second component comprising a first array of protrusions extending outwardly at least about 0.006 millimeter from the base surface component for receiving the discrete parts thereunto, a second array of suction ports preferably being disposed in the area having a roughened surface, and extending through the outer wall to an interior passage inside the transport head; taking, onto the roughened surface area, a discrete part having a textured surface wherein texture in the textured surface of the discrete part can interact with the roughened surface area of the transport head; where the suction ports are provided, optionally applying suction through the suction ports to the discrete part; and releasing the discrete part from the transport head and, where suction ports are optionally provided, from the suction ports.

The method further contemplates taking the discrete part as contained in a continuous web, and cutting the web to separate out the discrete part after the taking and before releasing the discrete part from the transport head.

The method also contemplates the transfer assembly being adapted to rotate about a first axis, to take the discrete part while the discrete part is travelling at a first speed, and to release the discrete part to a receiver travelling at a second speed, and includes rotating the transfer assembly about the first axis at a variable angular velocity such that the at least one transport head travels at a first surface speed which substantially equals the first speed of the discrete part as the discrete part is taken onto the at least one transport head in the taking zone, and travels at a second surface speed which substantially equals the second speed of the receiver as the discrete part is released to the receiver in the transfer zone, and further includes holding the discrete part to the transport head, optionally with suction, while rotating the rotatable transfer assembly from the taking zone to the transfer zone.

The method also preferably includes taking the discrete parts while the discrete parts are travelling in a first direction and transferring the discrete parts to the receiver while the receiver is travelling in a second direction, the transport head having an arcuate top wall for receiving the discrete parts thereunto, and including orienting the transport head such that the curvature of the arcuate top wall is disposed transverse to the first direction of travel at the taking zone, and after taking the discrete part onto the transport head, rotating the transfer assembly about a first axis oriented in a third direction transverse to, and disposed in a plane parallel with, the first direction, and rotating the transport head about a second radial axis intersecting the first axis, thereby aligning the arcuate top wall with the receiver at the transfer zone, such that after the rotation about the second radial axis, the arcuate top wall can interact with a substantially planar receiver disposed tangential to the orbital path, along a line transverse to the second direction in the transfer zone, and interacts with the discrete parts in the taking zone along a line approximating the first direction.

Finally, the fourth family of embodiments contemplates including taking the discrete part while the discrete part is elongated and under tension exerted by elastics integral with the discrete part, and holding the discrete part to the transport head with sufficient e.g. suction force that, when the elastics integral with the discrete part are elongated by e.g. 150%, in cooperation with a friction relationship between the transport head and the discrete part, the discrete part exhibits less than 50%, preferably less than 20%, more preferably less than 10%, snap-back of the elongation while the discrete part is held on the transport head.

A fifth family of embodiments comprehends apparatus for transferring discrete parts from a giver at a taking zone to a receiver at a transfer zone. The apparatus of this family comprises a transfer assembly; at least one transport head mounted on the transfer assembly, the transport head having an outer wall for taking the discrete parts, and for releasing the discrete parts, the outer wall having at least one area having a roughened surface, the at least one area comprising (i) a base surface component and (ii) a second component comprising a first array of protrusions extending outwardly at least about 0.006 millimeter from the base surface component, for receiving the discrete parts thereunto; and motive means for rotating the transfer assembly about an axis of rotation and thereby moving the at least one transport head from the taking zone to the transfer zone. The apparatus optionally includes a second array of suction ports, extending through the outer wall to an interior passage inside the transport head, and suction apparatus for applying suction to the at least one area through the second array of suction ports while the transport head is moving from the taking zone to the transfer zone.

In preferred members of this fifth family of embodiments, the motive means is adapted to rotate the transfer assembly about the first axis, to take the discrete part while the discrete part is travelling at a first speed, and to release the discrete part to a receiver travelling at a second speed, including rotating the transfer assembly about the first axis at a variable angular velocity such that the at least one transport head travels at a first surface speed substantially equal to the first speed of the discrete part at the taking zone, and travels at a second surface speed substantially equal to the second speed of the receiver at the transfer zone.

Preferably, the above recited axis of rotation comprises a first axis of rotation, the transport head being mounted for rotation about a second radial axis of rotation intersecting, and extending outwardly from, the first axis of rotation.

In a sixth family of embodiments, the invention contemplates apparatus for intermittently applying and releasing suction to a rotating suction head. The apparatus comprises a tubular conduit comprising a central suction supply line, the tubular conduit comprising an outer circumferential wall, and having a length; a slip ring mounted for rotation about the tubular conduit, while maintaining suction seal between the slip ring and the tubular conduit; an enclosure comprising a suction chamber sealed to the slip ring, for rotation about the tubular conduit along with the slip ring and for applying suction to parts to be held to an outer surface of the enclosure; a first array of suction ports in the outer circumferential wall of the tubular conduit extending partway, but less than all the way, about the outer circumference of the tubular conduit; and a second array of suction ports in the slip ring, longitudinally aligned along the length of the tubular conduit with the first array of suction ports such that, upon rotation of the slip ring about the tubular conduit, the first and second arrays of suction ports become aligned for transfer of suction from the tubular conduit to the suction chamber, through the first and second arrays of suction ports.

Preferably, the first array of suction ports in the tubular conduit is arranged about the circumferential wall of the tubular conduit such that the suction ports in the first array are aligned with ones of said suction ports in the second array, and thereby supply suction to the suction chamber, over an angle of rotation of the slip ring of at least about 30 degrees, and no more than about 330 degrees.

In preferred embodiments, the slip ring comprises a first slip ring, the apparatus including a second slip ring displaced longitudinally along the length of the tubular conduit from the first slip ring, preferably beside the first slip ring, mounted for rotation about the tubular conduit while maintaining suction seal between the second slip ring and the tubular conduit, the tubular conduit having a third array of suction ports, and the second slip ring having a fourth array of suction ports for cooperating with the third array of suction ports, to thereby supply suction to a second suction chamber mounted to the second slip ring, over an angle of rotation of the second slip ring of at least about 30 degrees, and no more than about 330 degrees.

In a seventh family of embodiments, the invention comprehends a method of transferring a discrete part from a taking zone to a transfer zone using a transfer assembly having a transport head mounted thereon, the transport head including a taking section for taking the discrete part onto the transport head, the taking section having a roughened surface for receiving the discrete part thereon. The method comprises the steps of taking a discrete part onto the transport head at the taking section; holding the discrete part on the transport head by interaction between a textured surface of the discrete part and a roughened surface of the taking section; orienting the taking segment such that the discrete part is disposed in a downward orientation such that gravity urges the discrete part to separate from the taking section, and wherein the interaction between the textured surface of the discrete part and the roughened surface of the taking section maintains the holding of the discrete part on the taking section; and transferring the discrete part away from the taking section and thus off the transport head, to a receiver, by applying an outside force to the discrete part.

In preferred embodiments, the method includes applying adhesive to the discrete part, and drawing the discrete part away from the transport head by contacting the adhesive with a substrate onto which the discrete part is transferred.

The method can include taking the discrete part as contained in a continuous web, and cutting the web to separate the discrete part from the web after taking the discrete part onto the transport head and before transferring the discrete part to the receiver.

The method further comprehends taking the discrete part while the discrete part is elongated and under tension exerted by elastics integral with the discrete part, and holding the discrete part to the transport head with sufficient force that, in cooperation with a friction relationship between the transport head and the discrete part, the discrete part exhibits less than 50% snap-back of the elongation while the discrete part is held on the transport head.

In preferred embodiments, the method includes enhancing the holding of the discrete part to the transport head by applying suction through the transport head and thus urging the discrete part toward the transport head.

Finally, the method comprehends that the orienting of the discrete part includes rotating the transfer assembly about a substantially horizontal axis and thereby orienting the discrete part downwardly within 30 degrees of the vertical before the transferring of the discrete part away from the transport head.

BRIEF DESCRIPTION OF THE DRAWINGS

The present invention will be more fully understood and further advantages will become apparent when reference is made to the following detailed description of the invention and the drawings, in which:

FIG. 2 representatively shows a schematic side view in elevation of the apparatus of FIG. 1.

DETAILED DESCRIPTION OF THE ILLUSTRATED EMBODIMENTS

The following detailed description is made in the context of a paper converting process. The invention can be appropriately applied to other flexible web processes.

The present invention provides methods and apparatus for taking discrete parts travelling at a first speed and transferring the parts to a substrate web travelling at a second speed. The methods and apparatus are particularly useful for taking parts of an elastic material, such as leg or waist elastic, and transferring the parts to a product such as, for example, a disposable diaper or other incontinence product. It is readily apparent, however, that the methods and apparatus would be suitable for applying any part to any suitable receiver.

Figure 1:
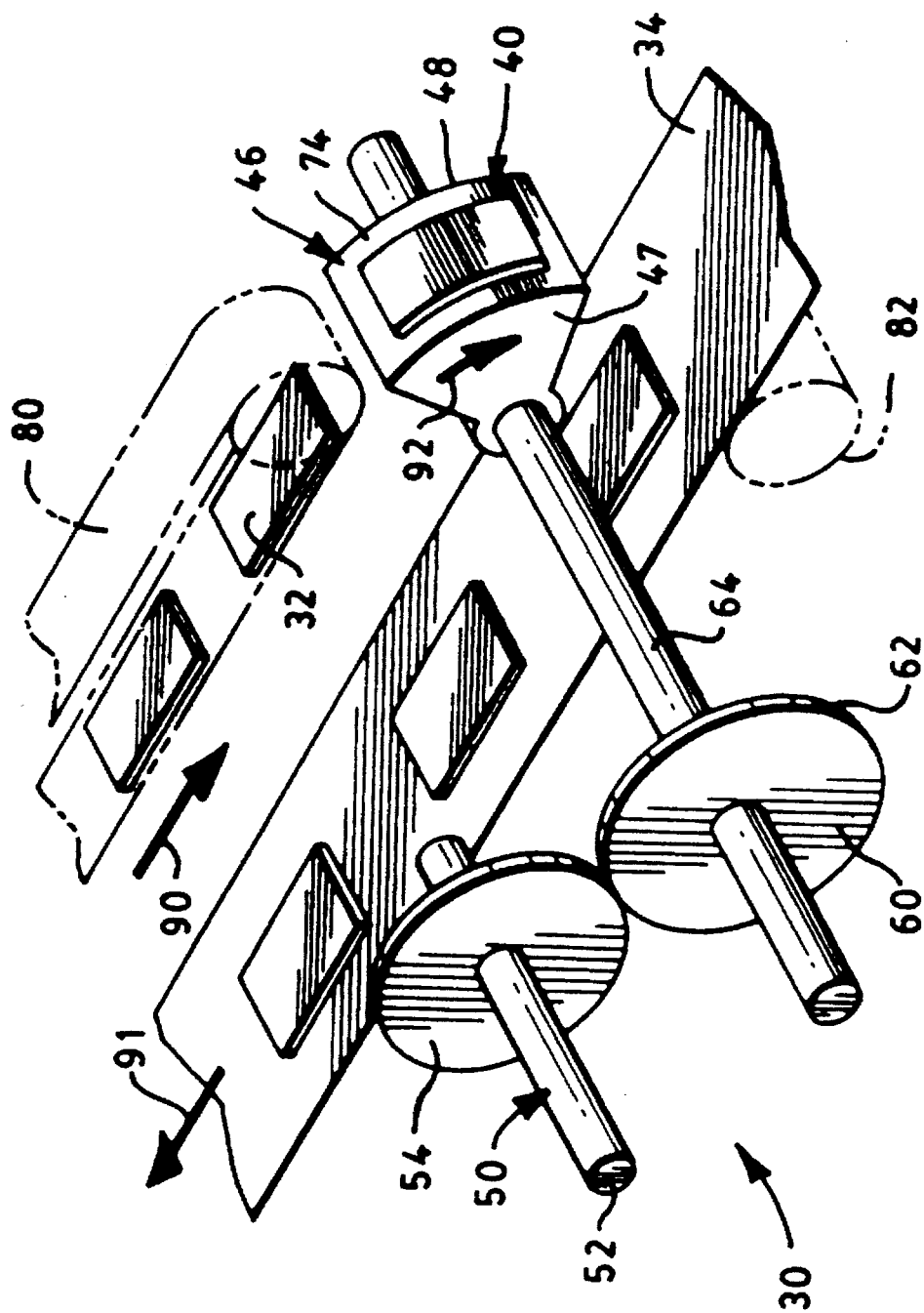
FIG. 1 representatively shows a pictorial view of one example of apparatus of the invention.

Referring now to FIGS. 1 and 2, there is representatively shown an aspect of the invention wherein apparatus generally indicated at 30 receives discrete parts 32 travelling at a first speed in the direction indicated by the arrow 90 associated therewith and applies the parts 32 to a substrate web 34 travelling at a second speed in the direction indicated by the arrow 91 associated with the substrate web. The illustrated example of the apparatus 30 comprises a rotatable transfer assembly 40 for receiving and applying the parts 32. The apparatus 30, as representatively shown in FIGS. 1 and 2, further comprises a driving means 50 for transmitting rotational energy to a driven means 60. The driving means 50 includes at least one rotatable noncircular drive gear 54 and the driven means 60 includes at least one rotatable noncircular driven gear 62. In use, the noncircular drive gear 54 engages and rotates the noncircular driven gear 62 which, in turn, rotates the transfer assembly 40.

The illustrated example of the transfer assembly 40 comprises at least one shell segment 48 connected to an output shaft 64. The shell segment 48 of the transfer assembly 40 may be connected to the output shaft 64 by any technique known to those skilled in the art such as, for example, bolts, screws, key and matching keyways, welding and the like or combinations thereof. For example, the shell segment 48 may be connected to the output shaft 64 by a key inserted into mating keyways in the shell segment 48 and output shaft 64. Similarly, the other components of the apparatus 30 of the present invention can be connected together employing the above described assembly techniques.

The shell segment 48, as representatively illustrated in FIGS. 1 and 2, can include a transport head 46 and a wall 47 connected to and extending perpendicularly from the transport head. The web member is also connected to the output shaft 64. The dimensions of the shell segment 48 will vary depending upon the desired output of the transfer assembly 40 and the size and shape of the discrete parts 32 being transferred. For example, the transport head 46 of the shell segment 48 may have an outer arcuate surface 74 spanning from about 20 degrees to about 340 degrees, a length of the outer arcuate surface of from about 1 inch to about 12 inches (about 25 mm to about 305 mm), and a width of from about 0.5 inch to about 20 inches (about 13 mm to about 512 mm). As the output shaft 64 rotates, the transfer assembly 40 travels in the direction indicated by the arrow 92 associated therewith. The outer arcuate surface 74 of the transport head, which is the circumferential, outer peripheral surface of the transfer assembly 40, travels along and defines an orbital path 75 that passes through a taking zone 42 and a transfer zone 44. The taking zone 42 and the transfer zone 44 are defined by the respective segments of the orbital path travelled by the outer arcuate surface 74 of the transfer assembly 40.

The illustrated example of the driving means 50 includes a rotatable noncircular drive gear 54 connected to an input shaft 52. The illustrated example of the driven means 60 includes a rotatable noncircular driven gear 62 connected to an output shaft 64. The output shaft 64 is parallel to, but offset from the input shaft 52, such that the noncircular drive gear 54 is configured to engage and rotate the noncircular driven gear 62. The driving means 50 may include a motor operatively connected through suitable gearing to the input shaft 52. Thus, in use, the motor rotates the input shaft 52 which rotates the noncircular drive gear 54 which, in turn, rotates the driven gear 62, output shaft 64 and transfer assembly 40.

Alternatively, the illustrated driven means 60 may include a noncircular driven gear 62 which is connected to a jackshaft instead of being connected to the output shaft 64. The term "jackshaft" connotes a rotatable shaft supported in two locations that is capable of receiving the rotational energy from the driving means 50 and transferring the energy to the output shaft 64. The jackshaft is parallel to but offset from the input shaft 52 such that the noncircular drive gear 54 is configured to engage and rotate the noncircular driven gear 62. The driven means 60 may further include a transmitting means, such as a pair of complementary gears connected to the jackshaft and output shaft 64 respectively, for conducting the rotational energy from the jackshaft to the output shaft 64 to rotate the output shaft 64 and the transfer assembly 40. Alternatively, the transmitting means may include any mechanism known to those skilled in the art by which rotational energy can be conducted from one shaft to another such as, for example, circular gears, v-belts, timing belts, continuous chains and the like or combinations thereof. Further, the transmitting means may include a second pair of complementary noncircular gears to provide additional speed variations.

Figure 3A:
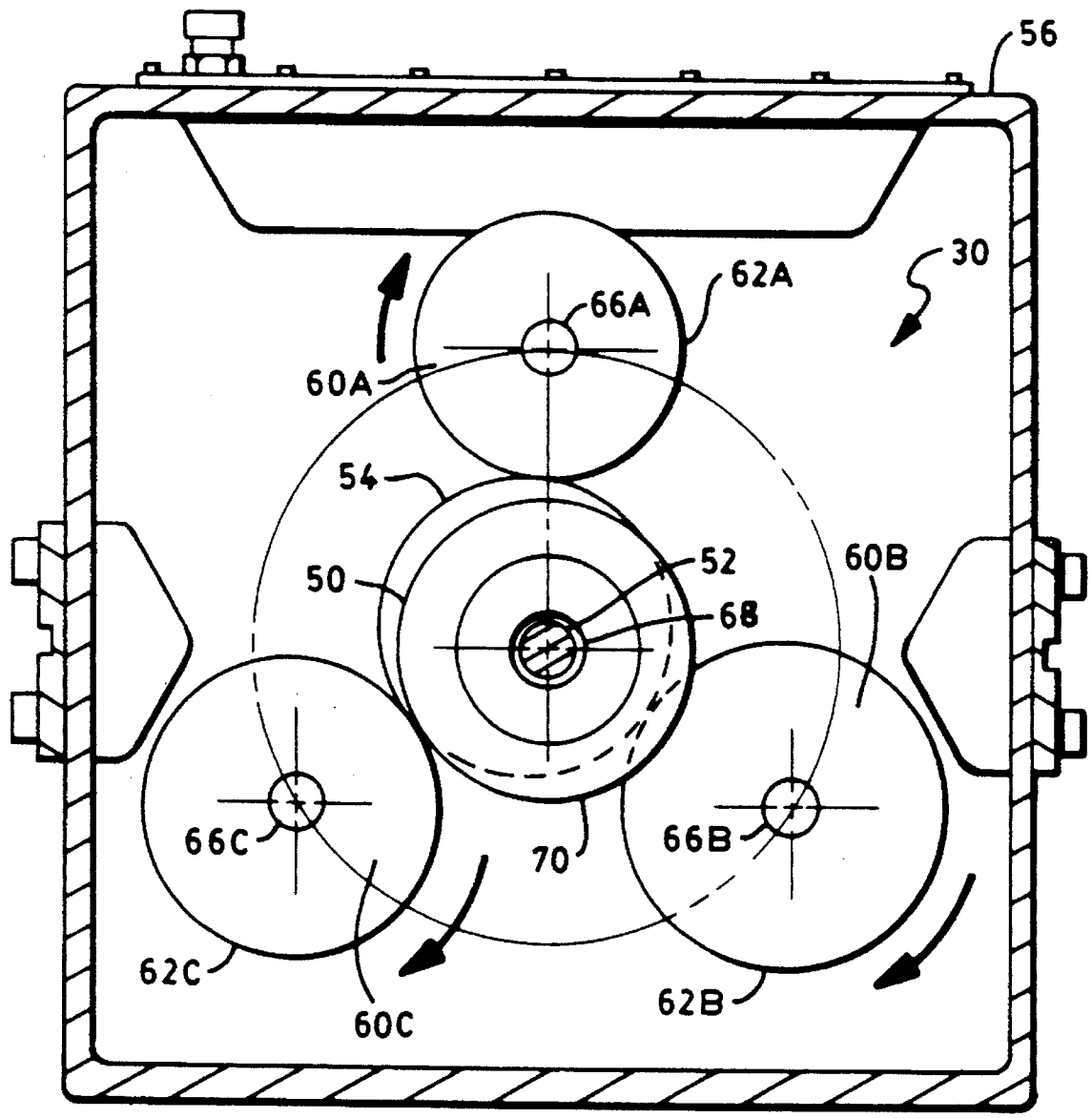
FIG. 3A representatively shows a schematic side view in elevation of another example of apparatus of the invention.
Figure 3B:
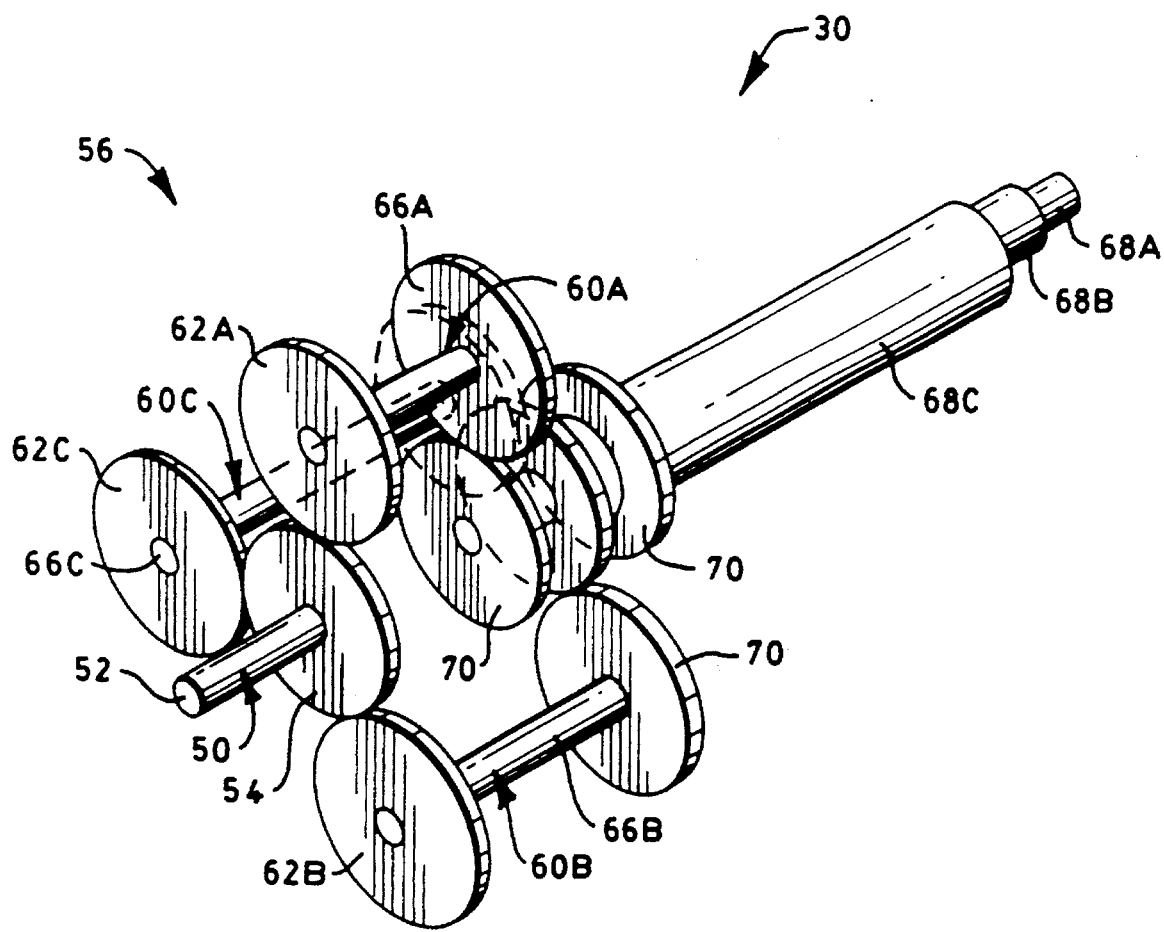
FIG. 3B representatively shows a pictorial view of the apparatus of FIG. 3A.

It will be further appreciated that the method and apparatus 30 of the invention can utilize one or, in the alternative, two, three or more combinations of transfer assembly 40 and driven means 60 in series to achieve the desired application of the discrete parts to the substrate web. The different combinations may allow the use of a continuously moving web to supply the discrete parts. In addition, greater speed ratio differentials may be achieved by using combinations of transfer assembly and driven means in series. For example, referring now to FIGS. 3A, 3B, 4 and 5, there is representatively shown another aspect of the invention wherein an apparatus generally indicated at 30 receives discrete parts 32 of a web of an elastic material 36 travelling at a first speed in the direction indicated by the arrow 93 associated with the web 36, and transfers the parts 32 to a substrate web 34 travelling at a second speed in the direction indicated by the arrow 94 associated with web 34. The illustrated example of the apparatus 30 comprises three shell segments 48, represented by 40A, 40B and 40C (FIGS. 4 and 5), for receiving and applying the parts 32. The apparatus 30 further comprises a gearbox 56, as representatively shown in FIGS. 3A and 3B, having a driving means 50 which includes a rotatable noncircular drive gear 54 for transmitting rotational energy to the three driven means 60, represented by 60A, 60B and 60C. The driven means 60, which includes a rotatable noncircular driven gear 62, represented by 62A, 62B and 62C, is configured to rotate each of the shell segments 48.

Figure 4:
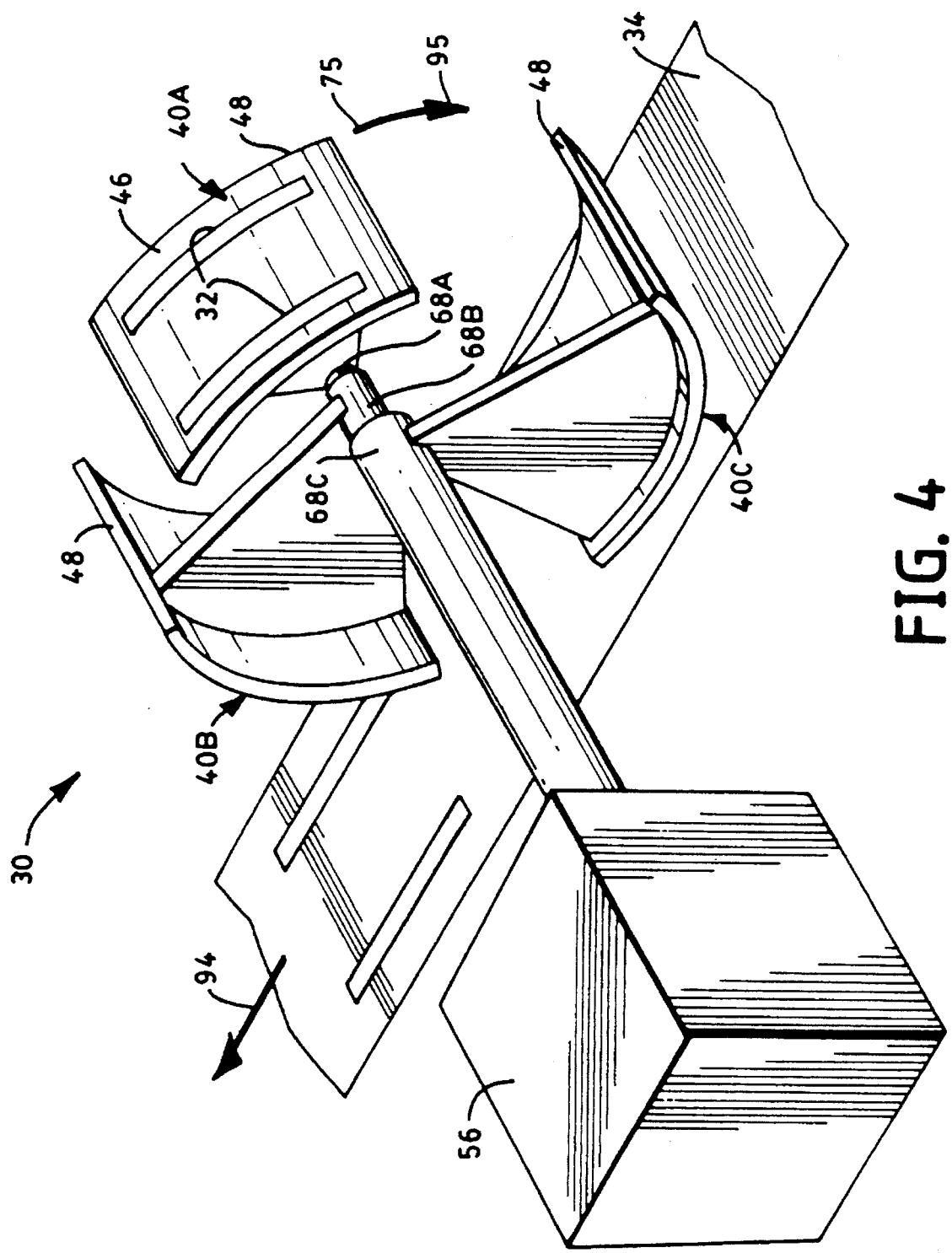
FIG. 4 representatively shows another pictorial view of the apparatus of FIG. 3A.
Figure 5:
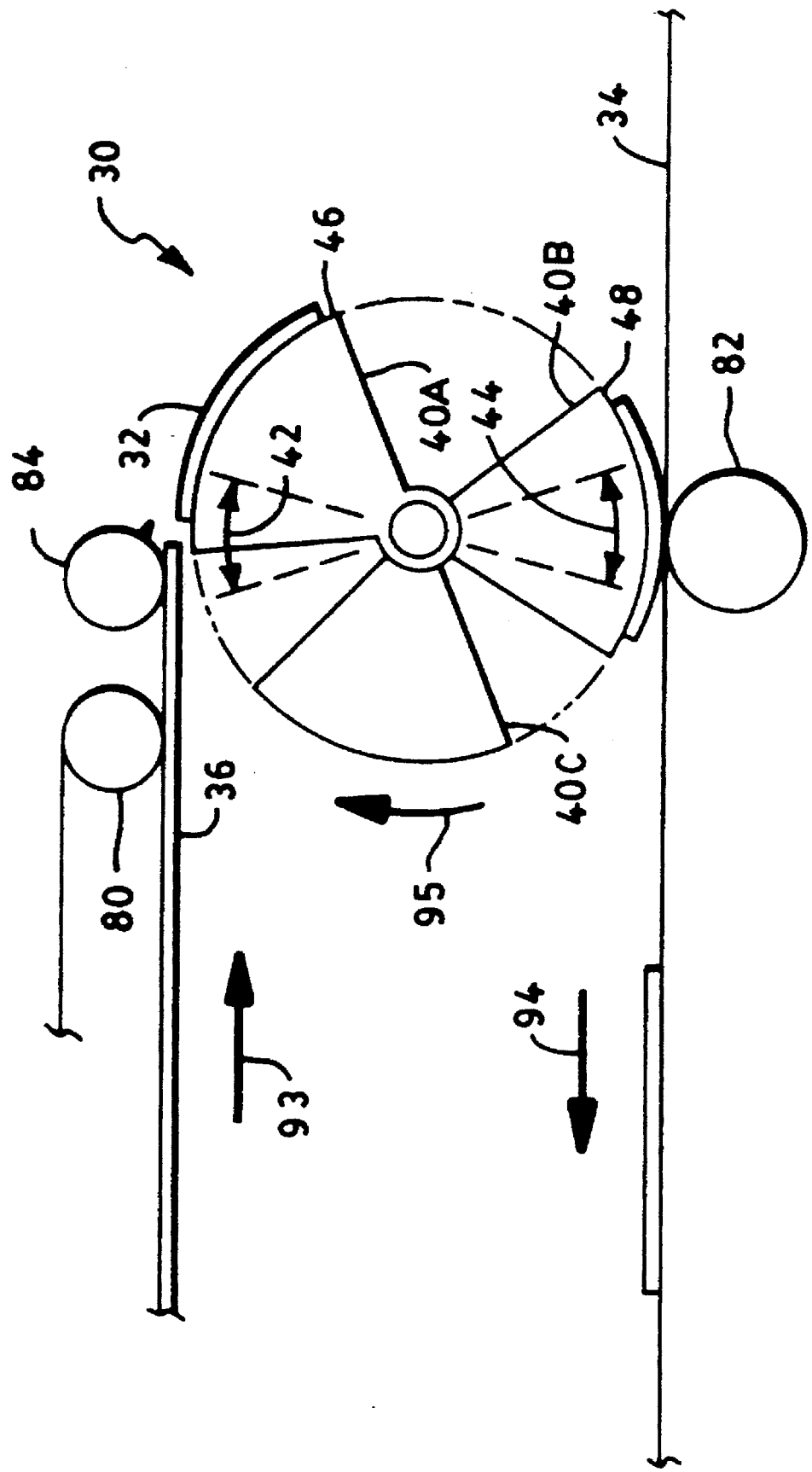
FIG. 5 representatively shows another schematic side view in elevation of the apparatus of FIG. 3A.

As illustrated in FIGS. 4 and 5, each of the shell segments 48 is connected to a concentric shaft 68, represented by 68A, 68B and 68C. As each concentric shaft 68 rotates, the transfer assembly 40 travels in the direction indicated by an arrow 95 associated with the transfer assembly. In use, the circumferential, arcuate outer surfaces 74 as seen in FIG. 1, of the respective shell segments 48A, 48B, and 48C travel along and define the orbital path 75 that passes through taking zone 42 and transfer zone 44. The taking zone 42 and the transfer zone 44 are defined by the respective segments of the orbital path travelled by the arcuate outer surfaces of the transfer assembly 40.

The size and shape of each shell segment 48 may vary as the number of shell segments per transfer assembly 40 changes. For example, if the apparatus includes three shell segments as representatively illustrated in FIGS. 4 and 5, each shell segment 48 may have an outer arcuate surface which spans from about 30 to about 120 degrees of the orbital path 75 of the transfer assembly 40.

As illustrated in FIGS. 3A, 3B, 4 and 5, the example of the driving means 50 includes the rotatable noncircular drive gear 54 connected to an input shaft 52. The illustrated example of each of the driven means 60 includes the corresponding rotatable noncircular driven gear 62 connected to a corresponding jackshaft 66, represented by 66A, 66B and 66C. Each jackshaft 66 is parallel to but offset from the input shaft 52 such that the noncircular drive gears 54 are configured to engage and rotate the respective noncircular driven gears 62 thereby rotating, the respective jackshafts 66. Thus, as illustrated, the single noncircular drive gear 54 is configured to engage and rotate the three noncircular driven gears represented by 62A, 62B and 62C which are respectively connected to the three jackshafts represented by 66A, 66B and 66C. Each driven means 60 may further include a transmitting means 70, as representatively illustrated in FIG. 3B, such as a pair of complementary gears connected to each jackshaft 66 and each concentric shaft 68 respectively, for conducting the rotational energy from each jackshaft 66A, 66B and 66C to the respective concentric shaft 68A, 68B and 68C thereby rotating the respective concentric shaft 68 and transfer assembly 40. Alternatively, the transmitting means 70 may include any mechanism known to those skilled in the art by which rotational energy can be conducted from one shaft to another such as, for example, circular gears, v-belts, timing belts, continuous chains and the like or combinations thereof.

Further, each transmitting means 70 may include a second pair of complementary noncircular gears to provide additional speed variations. Each transmitting means 70 may be connected to the respective jackshaft 66 and concentric shaft 68 by any technique known to those skilled in the art, such as those described above. For example, each transmitting means may include a pair of complementary gears connected to the respective jackshaft and concentric shaft by a key inserted into mating keyways in the jackshaft and concentric shaft.

In operation, the driving means 50 may include a motor operatively connected through suitable gearing to the input shaft 52. Thus, the motor rotates the input shaft 52 which rotates the noncircular drive gear 54 which, in turn, rotates the respective driven gears 62A, 62B and 62C and jackshafts 66A, 66B and 66C, which, in turn, rotate the respective concentric shafts 68A, 68B and 68C and shell segments 48A, 48B, and 48C.

The apparatus 30, as representatively illustrated in FIG. 5, may further comprise a pinch knife cutter 84 to sever the continuously moving web of elastic material 36 into discrete parts 32 that are fed onto each shell segment 48. The pinch knife cutter 84 may be any mechanism known to those skilled in the art that can sever a web of material into discrete segments such as, for example, a rotary cutter. It will be apparent that the continuously moving web of elastic material 36, in certain aspects of the invention, may be omitted and the discrete parts 32 may be placed directly upon the transfer assembly 40. In addition, it will be apparent that the parts 32 may be adhered to the substrate web 34 by means of an adhesive applied in a selected pattern to the surface of the parts 32, or by any other suitable means for adhering the parts to the substrate web 34.

The use of a noncircular drive gear 54 and a noncircular driven gear 62 in the apparatus 30, as representatively illustrated in the various aspects of the invention described above, provides an inexpensive and adaptable method for receiving discrete parts 32 travelling at a speed and transferring the parts to a substrate web 34 travelling at a different speed. To provide the variable angular velocity, the radius of the noncircular drive gear, or input gear, varies. Moreover, since the center to center distance between the noncircular gears remains constant, the radius of the noncircular driven gear, or output gear, changes to correspond to the variations in the radius of the input gear such that the gears remain engaged or meshed during rotation. The respective design of the noncircular gears can be controlled analytically to obtain the desired output function. For example, the speed profile of a typical set of complementary noncircular gears is representatively illustrated in FIG. 6. Thus, the combination of the complementary noncircular gears 54 and 62, as used to drive the transfer assembly 40 of the present invention, can provide variable angular velocity having periods where the velocity remains constant for a fixed duration. The fixed speed dwell can be advantageous when taking the discrete parts 32 onto the transport head 46 and when transferring them to the substrate web 34, particularly when the transfer occurs over a substantial arc length of contact.

Noncircular gears, such as those used in the present invention, can be purchased from Cunningham Industries, Inc. located in Stamford, Conn. Alternatively, one of ordinary skill in the art can manufacture the set of complementary noncircular gears if provided with the analytical representation of the desired output function as representatively illustrated in FIG. 6. For example, the design of a set of noncircular gears, as representatively shown in FIG. 7, can be developed as follows. First, the output function including the required process speeds and dwells must be laid out as in FIG. 6 to determine the proper radius of the orbital path that the transfer assembly follows and the proper gear ratios and gear angles for the noncircular gears. Secondly, the coefficients which establish the transition or acceleration/deceleration portions of the noncircular gears, as representatively illustrated in FIG. 7, must be computed. Once the angles, ratios and coefficients are known, the gear center to center distance is chosen from which follows the required radii for the noncircular gears.

Figure 6:
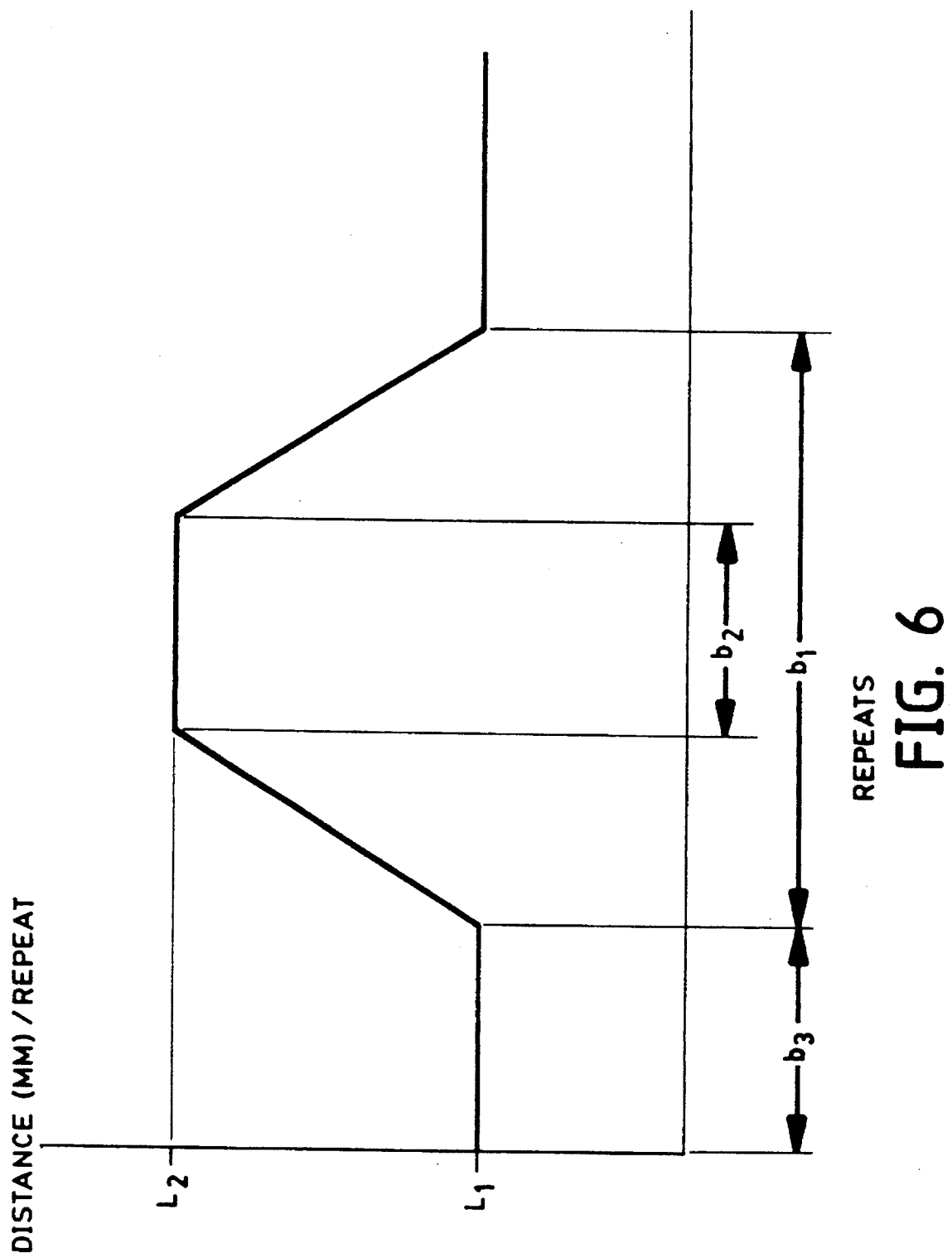
FIG. 6 representatively shows a speed profile for a typical set of complementary noncircular gears for the embodiment illustrated in FIGS. 3A, 3B, 4, and 5.

The radius of the orbital path is determined by calculating the total area under the output function curve as illustrated in FIG. 6. The equations for doing this are:

$$\text{Area} = L_1 + 0.5(b_1 + b_2)(L_2 - L_1) \tag{1}$$

$$R = \text{Area}/2\Pi \tag{2}$$

where:

R=radius of the orbital path (mm)

Area=area under the output function curve (mm)

$L_1$=low speed of the transfer assembly (mm/repeat)

$L_2$=high speed of the transfer assembly (mm/repeat)

$b_1$=total time during the trapezoidal portion of the curve (repeats)

$b_2$=total time to dwell at high speed (repeats)

$b_3$=total time to dwell at low speed (repeats)

Figure 7:
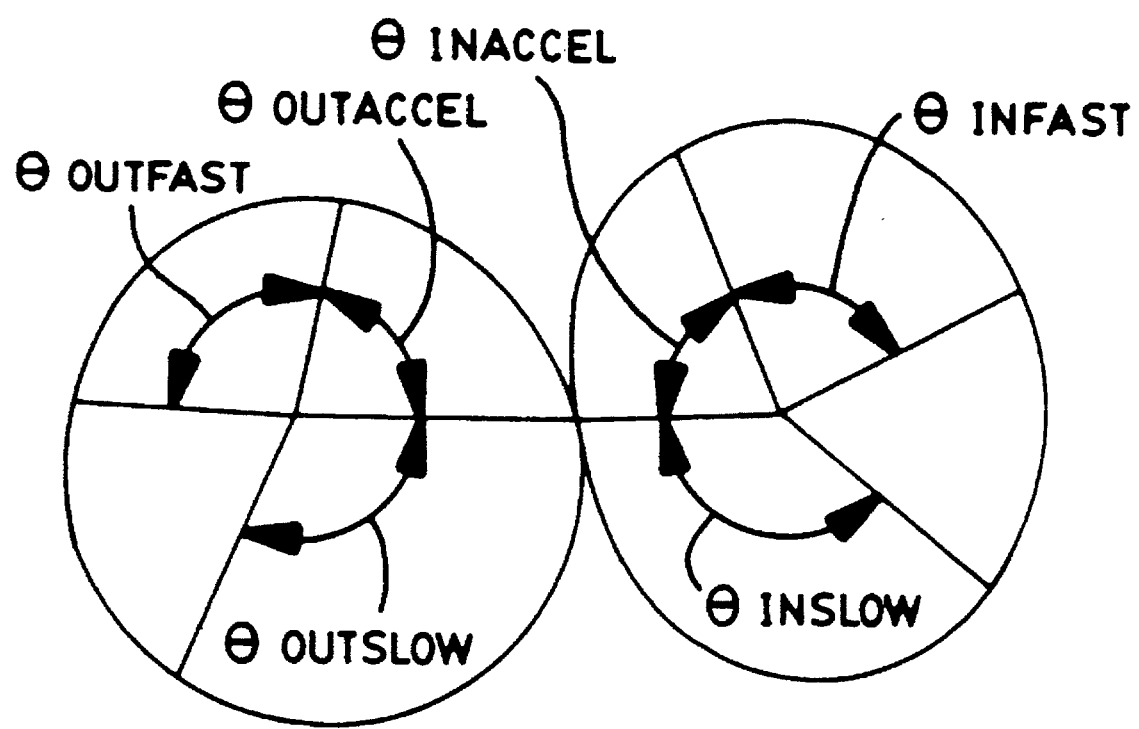
FIG. 7 representatively shows a schematic side view in elevation of a single noncircular gear set having designated angles of rotation.

Once the radius of the orbital path is determined, the ratios for the noncircular gears, as illustrated in FIG. 7, are determined as follows:

$$\theta\text{inslow} = 2\Pi b_3 \tag{3}$$

$$\theta\text{infast} = 2\Pi b_2 \tag{4}$$

$$\theta\text{inaccel} = 2\Pi(b_1 - b_2) \tag{5}$$

$$\theta\text{outslow} = (L_1 b_3)/R \tag{6}$$

$$\theta\text{outfast} = (L_2 b_2)/R \tag{7}$$

$$\theta\text{outaccel} = [2(b_1 - b_2)(L_1/2 + (L_2 - L_1)/4))]/R \tag{8}$$

$$\text{Slow speed ratio} = Y_1 = \theta\text{outslow}/\theta\text{inslow} = L_1/(2\Pi(R)) \tag{9}$$

$$\text{High speed ratio} = Y_2 = \theta\text{outfast}/\theta\text{infast} = L_2/(2\Pi(R)) \tag{10}$$

Once the proper ratios and angles have been chosen, the coefficients which define the shape of the noncircular gears can be computed. Gears designed with a sinusoidal function for the transition have been found to give good results in practice. The equation which defines the shape of the transitional part of the gears is given by:

$$\eta_{accel} = A - B \cos(C\theta) \tag{11}$$

where $\eta_{accel}$=ratio as a function of angular position during transition and $$A = (Y_1 + Y_2)/2 \tag{12}$$

$$B = (Y_2 - Y_1)/2 \tag{13}$$

$$C = 2\Pi/\theta\text{inaccel} \tag{14}$$

The actual pitch line radius of the noncircular gears can be determined once a choice has been made for the center to center distance between the noncircular gears. The gear radius is then given by:

$$R_{driven\ gear} = D_{center}/(1 + \eta_{accel}) \tag{15}$$

$$R_{drive\ gear} = D_{center} - R_{driven\ gear} \tag{16}$$

where:

$R_{driven\ gear}$=The radius of the noncircular driven gear $R_{drive\ gear}$=The radius of the noncircular drive gear $D_{center}$=The desired gear center to center distance By computing the ratios at any desired interval along the transition using equation (11) above, a smooth curve of the pitch line can be derived using equations (15) and (16). This smooth curve of the pitch line is used to construct a gear blank which is used to manufacture the noncircular gears.

Thus, the design of the profile of the complementary noncircular gears can be analytically determined to obtain the desired output function which can include variable angular velocities with fixed speed dwells. One must note that when two sets of complementary noncircular gears are used the output angles of the first set become the input angles of the second set. In addition, all of the angles on the gears must add up to $2\Pi$ radians or 360 degrees.

As compared to conventional methods, such as the slip gap method described above, for changing the speed of a discrete part such that it can be applied to a continuously moving web, the use of noncircular gears provides the ability to obtain greater changes in speed and to maintain constant speeds for a fixed duration. The fixed speed dwell achieved by using noncircular gears can be accurately and inexpensively designed to precisely control the length and placement of the discrete parts 32.

For example, in the various aspects of the invention, the profile of the noncircular gears 54 and 62 is analytically designed such that the rotatable transfer assembly 40 receives discrete the parts 32 in the taking zone 42 while maintaining a constant surface speed substantially equal to the incoming speed of the parts 32. Moreover, the profile of the noncircular gears 54 and 62 is designed such that the surface speed of the rotatable transfer assembly 40 changes to a second constant surface speed as the rotatable transfer assembly 40 moves from the taking zone 42 to the transfer zone 44. The term "surface speed," as used herein, refers to the speed of the circumferential, outer peripheral surface of the transfer assembly 40 as defined by arcuate outer surfaces 74 of the respective transport heads 46. The profile of the noncircular gears can be designed such that the speed of the discrete parts 32 being transferred is substantially equal to the speed of the substrate web 34 as the discrete parts are applied to the substrate web in the transfer zone 44. The surface speed of the transfer assembly 40 is maintained substantially constant in the taking zone 42 and the transfer zone 44 for from at least about 0 to about 300 degrees of rotation, desirably from about 10 to about 300 degrees of rotation, and more desirably from about 120 to about 240 degrees of rotation of the transfer assembly 40. In addition, the surface speed increase or decrease of the transfer assembly 40 as it moves from the taking zone 42 to the transfer zone 44 defines a speed ratio of from at least about 0.9:1 to about 20:1, desirably from about 0.9:1 to about 10:1, and more desirably from about 0.9:1 to about 4:1. The term "speed ratio", as used herein, defines the ratio of the surface speed of the transfer assembly 40 as the parts 32 are applied to the substrate web 34 to the surface speed of the transfer assembly 40 as the parts 32 are taken.

The transfer assembly 40, as representatively illustrated in the various configurations of the invention, includes the transport head 46, as representatively illustrated in e.g. FIGS. 1 and 5, to grip the discrete parts 32 in the taking zone 42 and to transport the parts to the transfer zone 44. In a particular aspect of the invention, the transport head 46 may include a suction means for providing a region of relatively low pressure. The suction means may include ports through which a suction may be selectively imposed. Thus, the suction may be activated in the taking zone 42 and deactivated in the transfer zone 44 as the part 32 is applied to the substrate web 34. In this manner, positive control is maintained over the parts 32 at all times during the transfer process since, in these embodiments, there is no time at which the parts are free of the holding action provided by the transport head 46. Alternatively, the transport head may include any conventional technique known to those skilled in the art for holding and releasing parts such as, for example, mechanical clamps, electrical clamps, magnetic clamps and the like or combinations thereof.

The various aspects of the apparatus 30 may further comprise an infeed conveyor 80 and an outbound article conveyor 82 as representatively illustrated in FIG. 1. The infeed conveyor 80 may supply the discrete parts 32 to the transfer assembly 40. The outbound article conveyor 82 may carry the substrate web 34.

The method and apparatus of the present invention may be used in the manufacture of articles such as diapers, training pants, and adult incontinence products, among other uses. The method and apparatus may be used to apply discrete parts or components, such as, for example, waist elastic, leg elastic, tapes, snaps and hook and loop materials to the diaper or incontinence product. Articles such as diapers and incontinence products are described, for example, in U.S. Pat. No. 4,704,116 issued Nov. 3, 1987, to Enloe; U.S. Pat. No. 4,798,603 issued Jan. 17, 1989, to Meyer et al.; U.S. Pat. No. 4,710,187 issued Dec. 1, 1987, to Boland et al.; U.S. Pat. No. 4,770,656 issued Sep. 13, 1988, to Proxmire et al.; and No. 4,762,521 issued Aug. 9, 1988 to Roessler et al.; the disclosures of which are incorporated herein by reference.

In a particular aspect, the apparatus 30 of the invention, such as the configurations representatively shown in FIGS. 3A, 3B, 4 and 5, may be used to apply parts of leg elastic to a disposable diaper. For example, a continuously moving web of elastic material 36 is fed into the pinch knife cutter 84. The pinch knife cutter 84 severs the web of elastic material 36 into discrete parts 32 which are fed onto the transfer assembly 40 in the taking zone 42. As transfer assembly 40 rotates, the parts of leg elastic 32 are held onto the transfer assembly 40 by transport head 46 which includes suction. The suction is activated in the taking zone 42 and deactivated in the transfer zone 44 as the parts 32 are transferred to the substrate web 34. The driving means 50 and driven means 60 which, in combination, rotate the transfer assembly 40 include a pair of complementary noncircular gears 54 and 62. The profile of the noncircular gears 54 and 62 is designed as described above such that, as the noncircular gears 54 and 62 and transfer assembly 40 rotate, the transfer assembly 40 maintains a substantially constant surface speed as the parts of leg elastic 32 are taken and transferred. For example, the transfer assembly 40 receives the parts of leg elastic 32 in the taking zone 42 while maintaining a constant surface speed substantially equal to the speed of the web of elastic material 36. The surface speed of the transfer assembly 40 then changes to a second constant surface speed such that the speed of the parts of leg elastic 32 being transferred is substantially equal to the speed of the diaper web 34 as the parts of leg elastic 32 are applied to the diaper web 34 in the transfer zone 44. The surface speed of the transfer assembly 40 is then changed back to substantially equal the speed of the web of elastic material 36.

The parts of leg elastic 32 being applied to the diaper web 34 may be made of any suitable material having elastic or stretchable properties. Examples of such materials include films or layers of natural rubber, synthetic rubber, or thermoplastic elastomeric polymers, and can be panels, or single, or multiple threads or filaments or ribbons thereof. These materials may also be heat-shrinkable or heat-elasticizable. Furthermore, these stretchable materials may be formed with gatherable layers, such as spunbonded polymer materials, as a stretch-bonded laminate. For example, a suitable stretch-bonded laminate comprises two gatherable layers of 0.4 ounce per square yard of spunbond polypropylene having therebetween a layer of meltblown elastic material such as a Kraton elastic in either layer form or separate threads of material having a basis weight of about 0.5 ounce per square yard. The layer of the elastomeric is stretched, the two layers of polypropylene then joined to the elastomeric layer, and upon relaxing the layers, the polypropylene layers gather. The materials may be breathable or nonbreathable.

Figure 8:
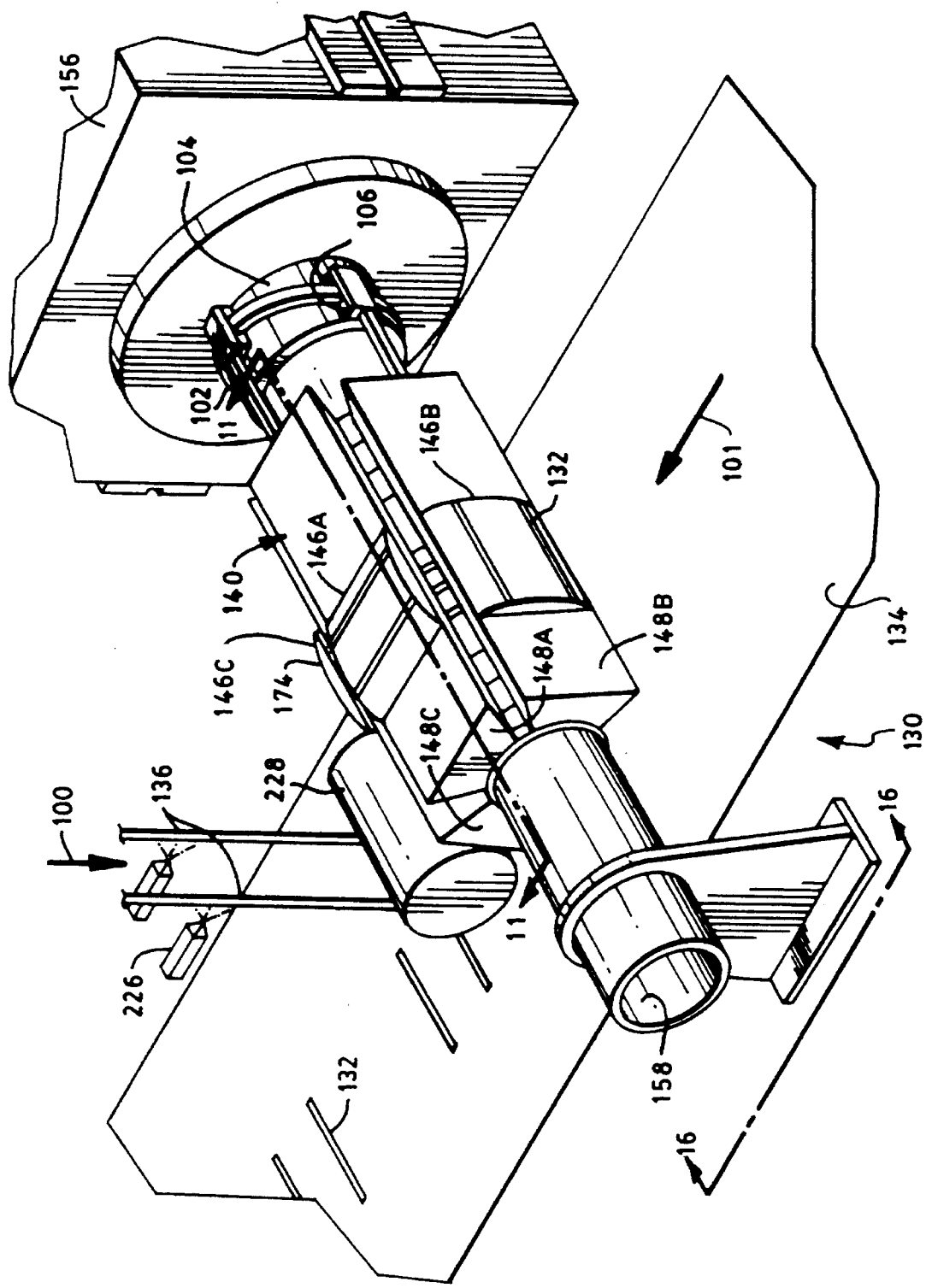
FIG. 8 shows a pictorial view of a further embodiment of apparatus of the invention.

Referring now to FIG. 8, there is representatively shown another aspect of the present invention wherein an apparatus generally shown at 130 receives discrete parts 132 as part of webs 136 travelling at a first speed in the direction indicated by the arrow 100 associated therewith and transfers the parts 132 to a substrate web 134 travelling at a second speed in the direction indicated by the arrow 101 associated therewith.

Figure 9:
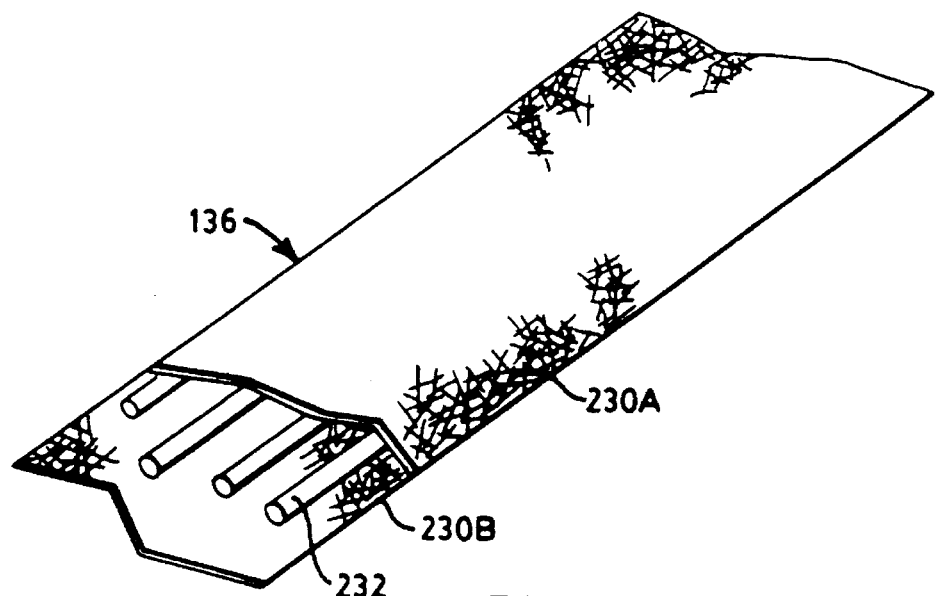
FIG. 9 shows a pictorial view, with parts cut away, of a portion of an incoming web to be transferred by apparatus of the invention.
Figure 10:
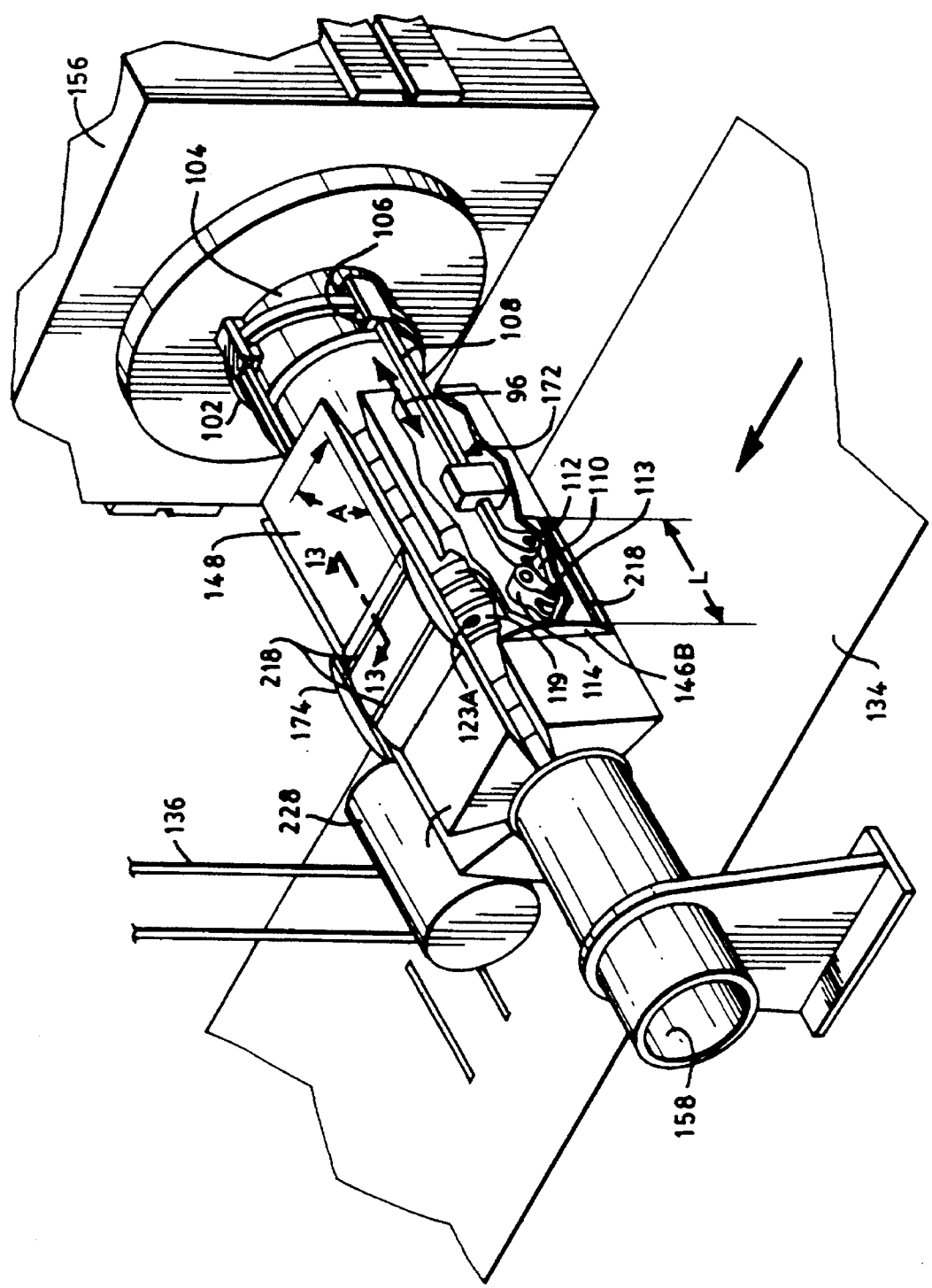
FIG. 10 shows an enlarged pictorial view of the embodiment of FIG. 8, with parts cut away to show the cam system and exemplary suction ports in a slip ring.

Referring to FIGS. 8–10, incoming webs of material 136 comprise first and second layers 230A and 230B of spunbonded polypropylene (0.7 ounces per square yard), and a plurality of threads 232 of elastic adhesively secured between the layers 230A and 230B. The elastic can be any of a variety of elastics suitable for providing the elastic property in the web 136. In a web 0.625 inch wide, suitable elasticity is provided by four threads of 940 decitex lycra generally uniformly spaced across the width of the web.

Figure 11:
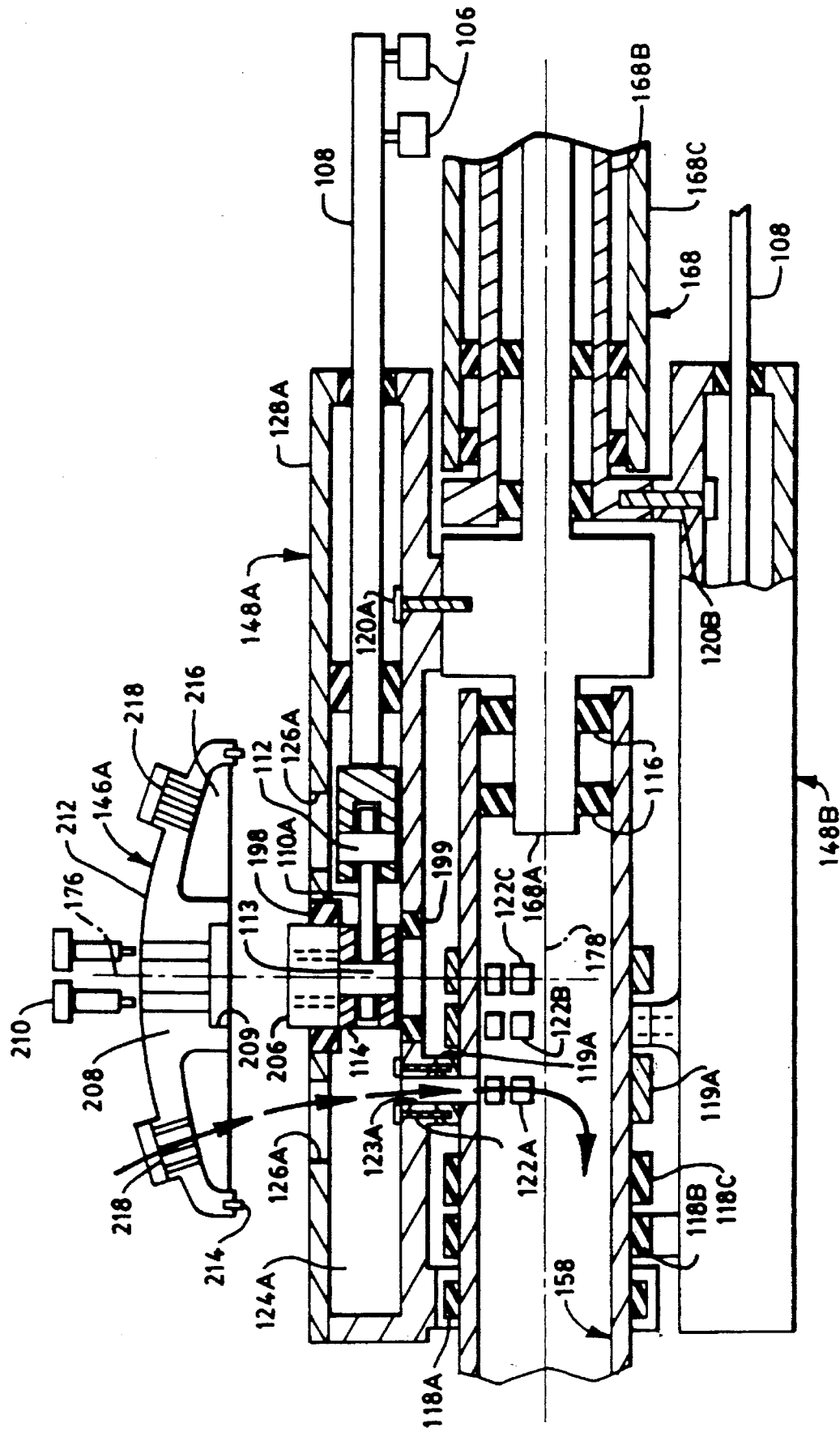
FIG. 11 is a sectional view taken at 11—11 of FIG. 8.

In the example illustrated in FIGS. 8 and 11, the rotatable transfer assembly 140 includes three shell segments 148A, 148B, and 148C, supported by concentric shaft 168 and tubular suction conduit 158.

Referring now to FIGS. 8–11 in combination, the drive system in gearbox 156, operating through concentric shaft 168, causes the shell segments 148A, 148B, and 148C to rotate about the concentric shaft 168 and tubular suction conduit 158. As the shell segments 148 rotate about a first generally horizontal axis 178 of the transfer assembly 140, a cam mechanism generally designated 172 rotates the transport head 146 about a radial axis 176 which intersects the generally horizontal axis 178 of the transfer assembly.

Figure 16:
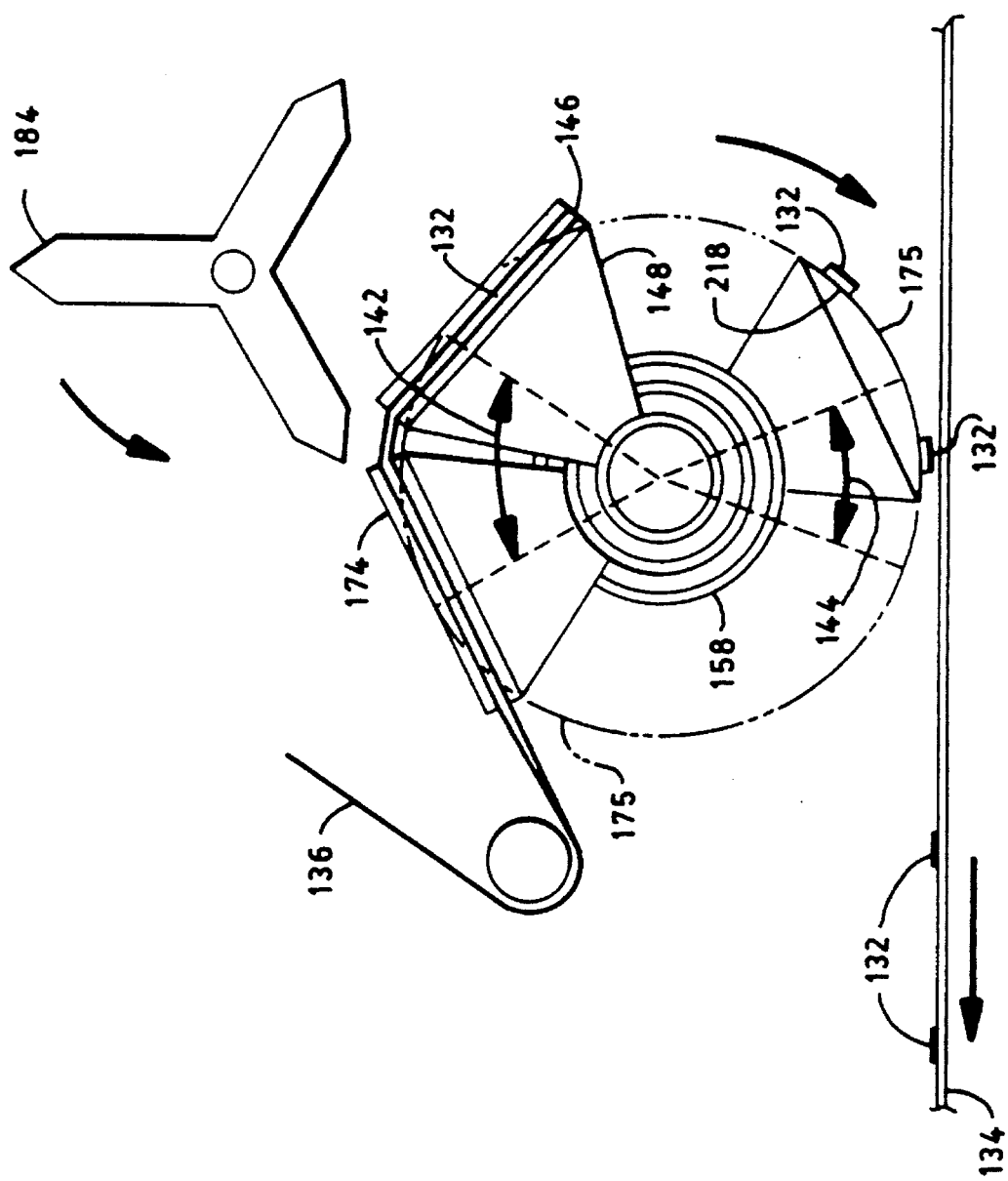
FIG. 16 is an elevation view generally taken at 16—16 of FIG. 8.

Accordingly, as shown in FIGS. 10, 11 and 16, starting from the taking zone 142, the arcuate top wall 174 of the transport head is disposed transverse to the direction of travel of the incoming web 136 of elastic material as the respective transport head picks up the incoming elastic material. The cam mechanism 172 then rotates the transport head 90 degrees about radial axis 176 by the time it reaches the transfer zone 144, and rotates it back the same 90 degrees by the time it returns to the taking zone.

Cam mechanism 172 includes an external cam 102 extending outwardly from, and circumferentially about, drum 104 which is fixedly mounted to the gearbox 156. A pair of cam followers 106 connected to each shell segment follows the cam 102 about the perimeter of the drum 104. Push rod 108 extends from cam followers 106 toward the respective transport head 146, and connects to actuating arm 110 through pin 112. Actuating arm 110 connects to the respective transport head 146 through pin 113 and crank clevis 114, as is discussed hereinafter. Accordingly, the reciprocating motion of push rod 108, as suggested by the double headed arrow 96, causes corresponding rotation of the respective transport head 146 as the respective shell segment 148 traverses the orbital path 175.

Referring especially to FIG. 11, the stationary tubular suction conduit 158 is mounted to the rotating concentric shaft 168 through shaft segment 168A and bearings 116. Shell segment 148A is mounted to tubular conduit 158 through bearing 118A. Similarly shell segments 148B and 148C are mounted to tubular conduit 158 through bearings 118B and 118C respectively.

Shell segment 148A is mounted to concentric shaft member 168A by bolt 120A. Similarly shell segments 148B and 148C are mounted to concentric shaft members 168B and 168C by bolts 120B, and 120C. Bolt 120C is not shown.

Slip ring 119A is bolted to shell segment 148A by bolts 121, and extends about, and is mounted for rotation about tubular suction conduit 158 at a fixed longitudinal location along the length of the conduit. A first array of suction ports 122A is disposed circumferentially about the outer wall of the conduit 158 along a portion of the path of rotation of slip ring 118A. FIGS. 10 and 11. A second array of suction ports 123A is disposed about a portion of the circumference of slip ring 119A adjacent shell segment 148A, and in alignment with the first array of suction ports in the conduit 158. Conventional suction seals (not shown) are used between the slip ring and the outer circumferential wall of the conduit 158. Accordingly, as the slip ring 119A rotates about conduit 158 with shell segment 148A, the second array of suction ports on the slip ring comes into alignment with the first array of suction ports on the conduit. Upon such alignment, suction is effected between conduit 158 and the interior chamber 124A of the shell segment 148A, as shown in FIG. 11. Correspondingly, the suction in the interior chamber 124A is transferred to transport head 146A through a third array of suction ports 126A in the top cover 128A of shell segment 148A.

Figure 12:
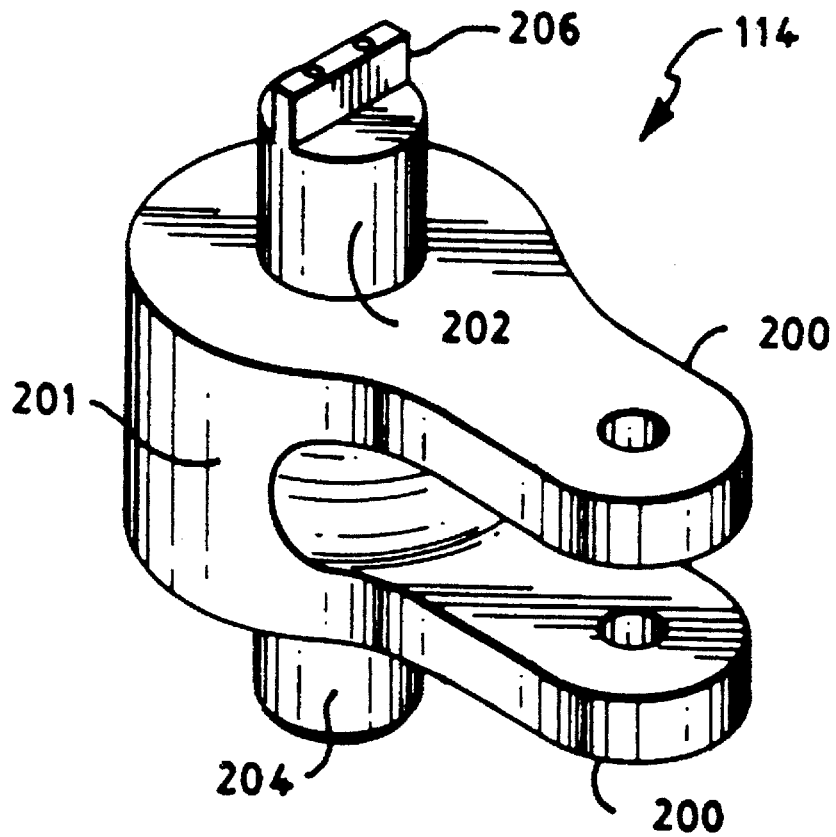
FIG. 12 is a pictorial view of the crank clevis which is actuated by the cam system.

Crank clevis 114 (FIG. 12) is mounted to shell segment 148A by upper and lower bearings 198, 199. A pair of arms 200 extend outwardly from the main body 201 of the crank clevis, for receiving the actuating arm 110A. A pair of upper and lower generally circular bearing posts 202, 204 extend upwardly and downwardly, respectively, from the upper and lower surfaces of arms 200 and engage the upper and lower bearings 198, 199. Male slot key 206 extends upwardly from the upper bearing post 202.

Transport head 146A has a main body 208. Female slot 209 corresponds with, and receives, male slot key 206 on the crank clevis 114. Transport head 146A is secured to crank clevis 114, through male slot key 206 and female slot 209, using a pair of bolts 210. Accordingly, when the female slot 209 is engaged with male slot key 206, rotational motion of the crank clevis 114 causes corresponding rotational motion in the transport head 146A.

The main body 208 of the transport head extends to an outer arcuate top wall 212, shown in FIG. 11. A suction seal 214 extends in a circular path, on transport head 146A, about the third array of suction ports 126A, providing a suction seal between the interior chamber 216 of the transport head and the top cover 128 of shell segment 148A. The third array of suction ports 126A is disposed radially about crank clevis 114, in a generally circular arrangement, such that suction in the interior chamber 124A of the shell segment is readily transmitted into the interior chamber 216 of the transport head.

The arcuate top wall 212 of the transport head 146 includes a taking section 218. Referring to FIGS. 10 and 13–15, each taking section 218 has a length "L" and a width "W", with the length being disposed in a direction transverse to the arc of the arcuate top wall 212, whereby each taking section 218 lies within generally a constant portion of the corresponding arcuate outer surface 174 along its entire length.

Figure 13:
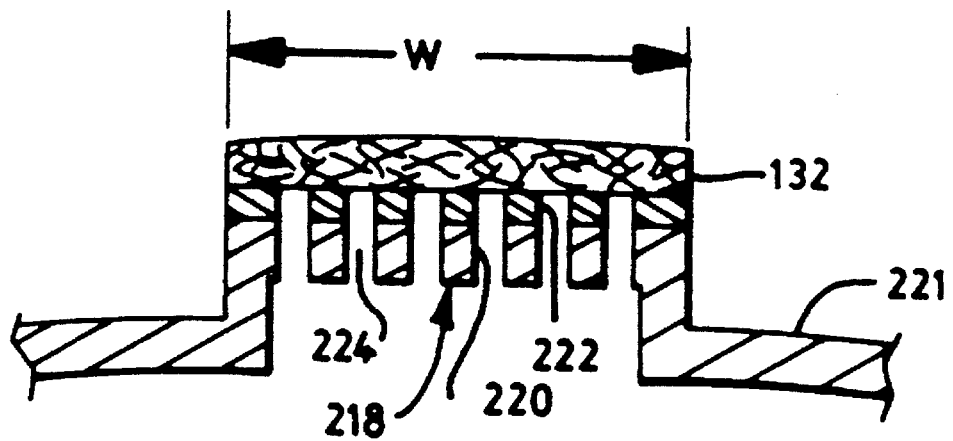
FIG. 13 is a cross section of the taking section of the outer wall of the transport head, with a discrete part thereon, taken at 13—13 in FIG. 10.

As seen in FIG. 13, each taking section 218 includes a substrate portion 220 extending above the main level 221 of the arcuate outer surface 174 of top wall 212 of transport head 146, and a toughened coating 222.

While not critical, and while no dimensions are considered controlling, the substrate portion 220 is preferably raised e.g. about 0.005 inch to about 0.125 inch above the main level 221 of the arcuate outer surface of the top wall 212, to facilitate performance of the taking sections. The roughened coating 222 can be characterized as any coating that provides a base surface component 223 overlying the substrate portion 220, and an array of protrusions 225 extending from the base surface component. The protrusions 225 extend at least 0.006 millimeter from the base surface component, with a range of about 0.01 millimeter to about 0.03 millimeter being preferred. Any upper limit to the length of the protrusions depends on the characteristics of the discrete parts to be transferred by the transport head. However, typically the protrusions will not extend more than about 3 millimeters from the base surface component.

In preferred embodiments, the roughened coating 222 has release characteristics at least as good as those of Teflon® polytetrafluoroethylene. However, a variety of release characteristics are acceptable, depending on the remainder of the process. A preferred coating is a plasma coating supplied as coating 902EA from Plasma Coatings, Inc., Waterbury, Conn.

The spacing between the protrusions 225 in the array of protrusions preferably is selected in view of the texture of the surface of the respective discrete part 132 which faces the transport head. The protrusions 225 should be spaced far enough apart to engage any surface texture of the discrete part, and close enough together to have sufficient engagement with elements of the parts 132 to provide a significant interaction between the elements of the parts and the protrusions on the coating. Thus, in applicants' contemplated application wherein the discrete parts are made with spun-bonded and like material, the protrusions should be spaced far enough apart that the fibers 227 can descend into the valleys 229 between the protrusions 225, and thereby engage the sidewalls of the valleys, to thereby fix the fibers, and correspondingly, the parts, in position on the taking sections 218.

"Textured surface" and "texture" of the surface of the parts 132 refers to any irregularities in the respective surface of the part that gives effective third dimension to the surface. Thus, for example, the fibers in nonwoven or woven fabrics comprise irregularities. Similarly, an emboss pattern in an otherwise smooth surface layer of film or nonwoven fabric would comprise a texture. Irregularities may be uniformly spaced as in a repeat emboss pattern or woven fabric, or spaced randomly as with nonwoven fibers.

The widths across the valleys in the projection matrix are necessarily less than the cross-sections of the fibers in the outer layers 230 of the webs 136 seen in FIG. 9. As the webs 136 are drawn onto the taking sections 218, the fibers 227 in the corresponding spunbonded outer layer 230 interact with the roughened surface provided by the plasma coating 222, wherein the individual fibers become drawn below the tops of the protrusions 225 and into the intervening valleys 229, thereby creating stresses in the matrix of the spunbonded material which interact with the protrusions on the corresponding taking section to hold the discrete parts securely in a fixed position on the taking section, and correspondingly, maintaining the existing elongation of the respective discrete parts.

Referring to FIGS. 11 and 13, an array of suction ports 224 extend through the substrate 220 and coating 222 of the taking section, thus applying the suction to the discrete parts as they are disposed on the outer arcuate surface (e.g. the taking sections 218) of the top wall 212 of the corresponding transport head 148.

As shown in the drawings, and especially referring to FIG. 11, shell segments 148B and 148C preferably correspond in general with the structure disclosed for shell segment 148A, with corresponding provision for bearings 118B and 118C, slip rings 120B and 120C, and concentric shafts 168B and 168C. Similarly the cam mechanism is preferably the same for all shell segments.

It is contemplated that the operation and functions of the invention have become fully apparent from the foregoing description of elements and their relationships with each other, but for completeness of disclosure, the usage of the embodiment illustrated in FIGS. 8–15 will be briefly described hereinafter.

Adhesive is applied to the incoming elastic webs of material 136 by adhesive applicators 226, and is cooled by turning roll 228, which also turns the elastic webs into alignment with the corresponding transport head 146C on the transfer assembly 140.

The surface driving speed of the transfer assembly is faster than the corresponding driving speed of the elastic thread unwind (not shown). Accordingly, in the embodiment shown, the elastic threads 232 are elongated up to about 300% from their relaxed length. Thus, the webs 136 are under tension exerted by the elastic threads 232 as the webs are taken onto the transport head 146C.

As seen in FIGS. 8–16, the arcuate outer surface 174 of the transport head is oriented transverse to the direction of travel of the incoming webs 136 at the respective transport head. Suction is activated on the taking sections of the transport head 146C as transport head 146C rotates into position to take the incoming webs onto its taking sections. As the transfer assembly continues to rotate about its horizontal axis 178, the taking sections of the transport head 146C take and hold corresponding portions of the webs 136, thus continuing the drawing of the webs 136 into the transfer assembly. Accordingly, the leading edge of each part 132 is oriented at an angle "A" transverse to the direction in which the part is travelling when the part is taken onto the transport head in taking zone 142.

As the transfer assembly 140 rotates under the driving force of the driving means 50 and the gearbox 156, the webs 136 are severed into individual discrete parts 132 by a heated knife or other cutter 184 as seen in FIG. 16.

Figure 14:
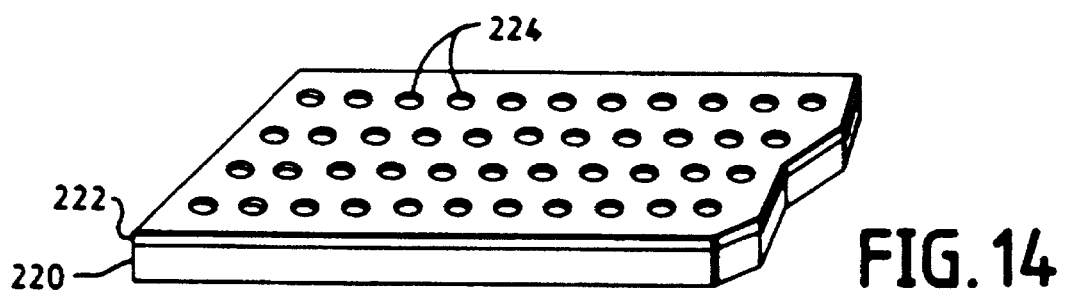
FIG. 14 is an enlarged fragmentary pictorial view of the surface of the taking section.
Figure 15:
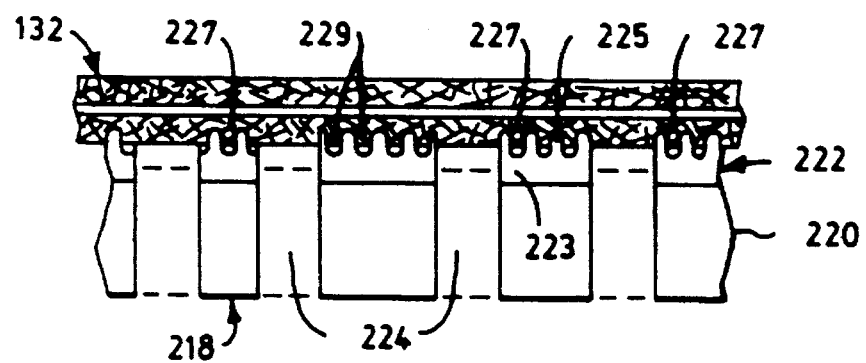
FIG. 15 is a cross-section as in FIG. 13, further enlarged to show the protrusions.

The elongation of the individual discrete parts is maintained by the combination of the protrusions 225 of the plasma coating 222 and the suction through the suction ports 224. FIG. 14 illustrates a typical suction port pattern for a taking section approximately 0.5 inch wide.

Without plasma coating 222, and using 45 inches of water, suction, the above web material 136, including layers 230A, 230B of 0.7 ounce per square yard spunbonded polypropylene and four threads of 940 decitex lycra, after being severed by heated cutter 184, exhibits greater than 10% snap-back. Using the plasma coating 222, and using only one inch water of suction, snap-back is less than 10% retracts to length shorter than 90% of the length, $L_1$, as shown in FIG. 6. Both the amount of suctions and the characteristics of the coating material 222 can be adjusted to affect the amount of snap-back tolerated by the specifications of the material being processed and the product being made. The amount of snap-back increases as the amount of suction is decreased. Snap-back also increases as the character of the coating material 222 changes to reduce the amount of entanglement between the fibers or other texturing of the surface of layers 230 and the protrusions 225.

While the plasma coating 222 is preferred, other types of coatings can be used to provide the protrusions 225. For example, conventional emery paper or the like can be used; but the corresponding emery paper substrate does not exhibit the beneficial long term wear characteristics of the plasma coating. So the plasma coating is preferred.

As the transfer assembly 140 continues to rotate, the transport head 146C moves around to the positions shown in FIG. 10 for transport heads 146A and 146B. By the time the transport head reaches the position shown for transport head 146B, the cam 102, acting through connecting linkages of cam follower 106, pushrod 108, actuating arm 110, pin 112, pin 113, and crank clevis 114 rotates the transport head such that it is oriented 90 degrees about the radial axis 176 to the position shown for transport head 146B in FIGS. 8 and 10, wherein the leading edge of the part is parallel to the direction of travel on the transfer assembly, and by the time the discrete part 132 reaches receiving web 134, parallel to the direction of the receiving web. At about the position shown for transport head 146B in FIG. 8, the non-circular gears in gearbox 156 cause an increase in the radial velocity of the corresponding transport head as described above with respect to FIGS. 6 and 7. By the time the transport head reaches the receiving web 134 at the transfer zone 144, the surface speed of the discrete parts 132 generally corresponds with the surface speed of the web 134.

Adhesive applied at adhesive applicators 226 is then activated. As the discrete parts 132 contact the web 134, the suction is released as the corresponding slip ring reaches the end of the corresponding array of suction ports 122 in the conduit, and the adhesive attraction between the discrete parts 132 and the web 134 causes the discrete parts to transfer to the receiving web 134.

The noncircular gears then cause a decrease in the radial velocity of the corresponding transport head such that, by the time the transport head returns to the taking zone 142 and to receive another portion of the incoming web 136, the surface speed of the transport head matches the surface speed of the incoming webs 136. As the transport head again picks up a portion of the incoming web 136, the corresponding slip ring 118 reaches the beginning of the corresponding array of suction ports 122 in the conduit, thereby activating suction on the corresponding transport head, to begin another cycle.

As used herein, "transverse" direction, when referring to rotation of the discrete parts means anything not aligned with the first direction of travel of the receiving web 36 or 136, and not 180° from the first direction.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. Apparatus for taking discrete parts traveling at a first speed in a first direction in a taking zone and transferring the discrete parts to a receiver traveling at a second speed in a second direction in a transfer zone, said apparatus comprising:

a transfer assembly mounted on a shaft for rotation about a first axis oriented in a third direction transverse to and disposed in a plane parallel with the first direction, said transfer assembly including a shell segment supported by said shaft and at least one transport head rotatably mounted on said shell segment for taking the discrete parts in the taking zone, wherein a leading edge of the discrete parts are oriented at a first angle with respect to the first direction of travel, and for transferring the discrete parts to the receiver in the transfer zone;

first driver means for rotating said transfer assembly about said first axis at a variable velocity so that said transport head travels substantially at the first speed as the discrete parts are taken onto the transport head in the taking zone, and travels at the second speed as the discrete parts are applied to the receiver in the transfer zone; and means for transferring drive from said first driver means to said transport head comprising a cam drive means, input shaft and output means, said cam drive means having a cam circumferentially secured to a drum affixed to a gear box and a cam follower movably affixed to said cam, said output means having an actuating arm movably connected to said transport head through a crank clevis wherein said transferring drive means rotates said transport head about a second axis transverse to said first axis to thereby orient the leading edge of the discrete part at a second angle different from the first angle as measured with respect to the second direction of travel of the receiver in the transfer zone.

2. The apparatus of claim 1 further comprising means for retaining said discrete parts engaged against said transport head from the taking zone until said discrete parts are transferred at the transfer zone.

3. The apparatus of claim 2 wherein said retaining means includes vacuum means for providing vacuum to said transport head.

4. The apparatus of claim 3 wherein said transport head comprises an arcuate top wall transversely oriented relative to said first direction, said arcuate wall including a taking portion having a roughened surface and at least one suction port for communicating vacuum from said vacuum means to said discrete parts while said discrete parts are engaged against said transport head from the taking zone until said discrete parts are transferred at the transfer zone.

5. The apparatus of claim 4 wherein said roughened surface includes a base surface component and an array of protrusions extending at least about 0.006 millimeters from said base surface component.

6. The apparatus of claim 2 wherein said first driver means includes the gear box comprising a second driver means and a driven means which in combination rotate said transfer assembly, said second driver means and said driven means includes a pair of complementary noncircular gears.

7. The apparatus of claim 1 wherein said second axis of rotation is substantially perpendicular to said first axis of rotation.

8. The apparatus of claim 4 wherein said vacuum means includes control means for applying and removing said vacuum to and from said taking portion of said transport head.

9. The apparatus of claim 8 wherein said control means includes:

(a) a slip ring fixedly secured to said shell segment and movably mounted for rotation about an outer circumferential wall of a tubular conduit;

(b) a first array of suction ports in said outer circumferential wall along a portion of a path of rotation of said slip ring; and (c) a second array of suction ports circumferentially disposed about a portion of said slip ring so that said second array suction ports become aligned with said first array suction ports as said slip ring rotates about said tubular conduit, thereby supplying suction to said taking portion of said transport head.

10. The apparatus of claim 9 wherein said vacuum means applies suction to said taking portion of said transport head through an arc of rotation of at least about 30 degrees to about 330 degrees.

11. The apparatus of claim 10 wherein said vacuum means applies suction to said taking portion of said transport head through an arc of rotation that substantially coincides with the rotation of said transport head from the taking zone to the transfer zone.

12. Apparatus for taking discrete parts traveling at a first speed in a first direction in a taking zone and transferring the discrete parts to a receiver traveling at a second speed in a second direction in a transfer zone, said apparatus comprising:

a transfer assembly mounted on a shaft for rotation about a first axis oriented in a third direction transverse to, and disposed in a plane parallel with, the first direction, said transfer assembly including a shell segment supported by said shaft and at least one transport head rotatably mounted on said shell segment for taking the discrete parts in the taking zone and for transferring the discrete parts to the receiver in the transfer zone, wherein a leading edge of the discrete parts are oriented at a first angle with respect to the first direction of travel;

first driver means for rotating said transfer assembly about said first axis at a variable velocity so that said transport head travels substantially at the first speed as the discrete parts are taken onto the transport head in the taking zone, and travels at the second speed as the discrete parts ere applied to the receiver in the transfer zone, said first driver means includes a gear box comprising a second driver means and a driven means which in combination rotate said transfer assembly, said second driver means and said driven means including a pair of complementary noncircular gears;

means for transferring drive from said first driver means to said transport head to rotate said transport head about a second axis transverse to said first axis to thereby orient the leading edge of the discrete part at a second angle different from the first angle as measured with respect to the second direction of travel of the receiver in the transfer zone; and vacuum means for providing vacuum to said transport head having control means for applying and removing vacuum to and from said taking portion of said transport head, said control means includes:

slip ring fixedly secured to said shell segment and movably mounted for rotation about an outer circumferential wall of a tubular conduit;

first array of suction ports in said outer circumferential wall along a portion of a path of rotation of said slid ring; and second array of suction ports circumferentially disposed about a portion of said slip ring so that said second array suction ports become aligned with said first array suction ports as said slid ring rotates about said tubular conduit, thereby supplying suction to said taking portion of said transport head.

13. The apparatus of claim 12 wherein said transport head comprises an arcuate top wall transversely oriented relative to said first direction, said arcuate wall including a taking portion including a base surface component and an array of protrusions extending at least about 0.006 millimeters from said base surface component, said taking portion further including at least one suction port for communicating vacuum from said vacuum means to said discrete parts while said discrete parts are engaged against said transport head from the taking zone until said discrete parts are transferred at the transfer zone.

14. The apparatus of claim 12 wherein said transferring drive means includes:

(a) a drum affixed to said gear box;

(b) a cam circumferentially secured to said drum;

(c) a cam follower movably affixed to said cam; and (d) an actuating arm movably connected to said transport head and said cam follower.

\* \* \* \* \*